(12) United States Patent
Mon

(10) Patent No.: US 8,476,242 B2
(45) Date of Patent: Jul. 2, 2013

(54) PRE-CONDITIONING/FIXATION FOR DISEASE TREATMENT HEAT ACTIVATION/RELEASE WITH THERMO-ACTIVATED DRUGS AND GENE PRODUCTS

(75) Inventor: John Mon, Silver Spring, MD (US)

(73) Assignee: Medifocus, Inc., Columbia, MD (US)

(*) Notice: Subject to any disclaimer, the term of this patent is extended or adjusted under 35 U.S.C. 154(b) by 1010 days.

(21) Appl. No.: 11/527,688

(22) Filed: Sep. 27, 2006

(65) Prior Publication Data

US 2007/0077230 A1    Apr. 5, 2007

Related U.S. Application Data

(63) Continuation-in-part of application No. 11/280,199, filed on Nov. 17, 2005, which is a continuation-in-part of application No. PCT/US2006/010505, filed on Mar. 2, 2006.

(60) Provisional application No. 60/664,699, filed on Mar. 24, 2005.

(51) Int. Cl.
*A61K 33/00* (2006.01)

(52) U.S. Cl.
USPC ............ 514/44 R; 424/93.1; 435/320.1

(58) Field of Classification Search
None
See application file for complete search history.

(56) References Cited

U.S. PATENT DOCUMENTS

| | | | |
|---|---|---|---|
| 4,565,200 A | | 1/1986 | Cosman |
| 5,496,271 A | | 3/1996 | Burton et al. |
| 5,620,479 A | * | 4/1997 | Diederich ............... 601/3 |
| 5,697,909 A | * | 12/1997 | Eggers et al. ............ 604/114 |
| 5,810,888 A | * | 9/1998 | Fenn ........................ 607/154 |
| 5,868,740 A | * | 2/1999 | LeVeen et al. ........... 606/41 |
| 5,928,229 A | | 7/1999 | Gough et al. |
| 6,059,780 A | | 5/2000 | Gough et al. |
| 6,235,023 B1 | | 5/2001 | Lee et al. |
| 6,241,725 B1 | * | 6/2001 | Cosman ..................... 606/41 |
| 6,690,976 B2 | * | 2/2004 | Fenn et al. ................ 607/101 |
| 2002/0072742 A1 | | 6/2002 | Schaefer |
| 2003/0152517 A1 | | 8/2003 | Peyman |
| 2003/0212394 A1 | * | 11/2003 | Pearson et al. ............ 606/41 |
| 2004/0044385 A1 | | 3/2004 | Fenn et al. |
| 2004/0249261 A1 | * | 12/2004 | Torchia et al. ............ 600/411 |

FOREIGN PATENT DOCUMENTS

| | | |
|---|---|---|
| WO | WO-99/00144 | 1/1999 |
| WO | WO-03/070298 | 8/2003 |
| WO | WO 2004/022159 A1 | 3/2004 |
| WO | WO 2005/007000 A1 | 1/2005 |
| WO | WO-2006/102471 | 9/2006 |

OTHER PUBLICATIONS

Goldberg, 2001, European Journal of Ultrasound, 13: 129-147.*
*Notification Concerning Transmittal of International Preliminary Report on Patentability* dated Oct. 4, 2007 issued in corresponding PCT patent application No. PCT/US2006/010505 together with the Written Opinion of the International Searching Authority and the International Search Report.
*Notification of Transmittal of the International Search Report and the Written Opinion of the International Searching Authority, or the Declaration* (together with the International Search Report and the Written Opinion of the International Searching Authority) dated May 14, 2007 issued in corresponding PCT patent application No. PCT/US2006/037569.
John N. Weinstein et al, "Treatment of Solid L1210 Murine Tumors with Local Hyperthermia and Temperature-sensitive Liposomes Containing Methotrexate", Cancer Research 40, 1388-1395, May 1980.
Final Office Action dated Dec. 11, 2009 in connection with U.S. Appl. No. 11/280,199, filed Nov. 17, 2005.

* cited by examiner

*Primary Examiner* — Deborah Crouch
(74) *Attorney, Agent, or Firm* — Merek, Blackmon & Voorhees, LLC

(57) ABSTRACT

A method of treating cancer by introducing heat into cancerous tissue and delivering a liposome containing an active agent or a thermo-activated drug, gene or virus to said tissue. The heat delivered is sufficient to release the active agent or activate the thermo-activated drug, gene or virus. The cancer can be esophageal cancer. The liposome containing an active agent or a thermo-activated drug, gene or virus can be a thermosensitive liposome. The active agent can be an antineoplastic agent, for example doxorubicin.

26 Claims, 19 Drawing Sheets

DYNAMIC CONTROL OF HEAT W/RIGID TEMPERATURE FORMULATION
RELEASE/ACTIVATED DRUGS AND/OR GENES AND/OR VIRAL VECTORS

DYNAMIC AND/OR STATIC AND/OR STEADY STATE HEATING PROFILE WITH BROAD TEMPERATURE FORMULATION RELEASE/ACTIVATION DRUGS AND/OR GENES AND/OR VIRAL VECTORS

45° C ELECTRODE TEMPERATURE. DASHED LINE SHOWS
DIRECTION OF DISTANCE MEASUREMENT

50° C ELECTRODE TEMPERATURE

60° C ELECTRODE TEMPERATURE

70° C ELECTRODE TEMPERATURE

80° C ELECTRODE TEMPERATURE

PRE-CONDITIONING/FIXATION FOR DISEASE TREATMENT HEAT ACTIVATION/RELEASE WITH THERMO-ACTIVATED DRUGS AND GENE PRODUCTS

CROSS REFERENCE TO RELATED APPLICATIONS

This application is a continuation-in-part of U.S. application Ser. No. 11/280,199 which claims the benefit of priority of U.S. Provisional Application No. 60/664,699, filed on Mar. 24, 2005, the subject matter of which is incorporated herein by reference.

BACKGROUND OF THE INVENTION

1. Field of the Invention

The present invention generally relates to an apparatus and a method for administering a focused energy treatment to a limited, defined area of a patient's body. The energy treatment can be delivered by the use of one or more energy applicators. The energy applicators can be used to trigger the release of active agents such as pharmaceutically active agents, nutritional agents, diagnostic agents, cosmetic agents, imaging agents, polynucleotides, and the like from liposomes and/or nanoparticles, in particular thermosensitive liposomes or nanoparticles, for the treatment of cancerous, precancerous, and benign lesions, as well as infectious diseases. The energy applicators can also be used to activate thermo-activated drugs, genes, and viral vectors for treatment of the same disease states.

2. Description of the Prior Art

In order to treat a specific treatment site, such as liver, prostate, breast, head and neck, bone, lungs, brain, pancreas, kidney, thyroid, esophageal or other localized solid or defused neoplasms, lesions and tumors, prior art methods have used focused heating devices such as Radio Frequency Ablation (RFA), Microwave Ablation (MA), Laser Ablation (LA), Ultrasound Ablation (UA), High Intensity Focused Ultrasound (HIFU), or focused microwaves (FM) used as a single modality. The previous uses of these treatments were limited in focus to small effective treatment regions. Recurrent tumors often occurred at the margins of a previously treated tumor. There may be ineffective cold spots throughout the treatment zone due to the non-homogeneous nature of these previous heating methods. The use of modalities such as RFA can indeed effectively heat a small defined area of tissue, but this area is limited to tissue in close proximity to a deployed heating antenna. This area is usually only within 1 to 2 centimeters of the heating antenna. Prior heat treating apparatuses have resulted in unsatisfactory tumor control, generally limited to the immediate center of the treatment site. As a consequence, significant tumor recurrence or continued growth of the cancerous tumors are common. Accordingly, there is a major need to increase the therapeutic kill zone over that of the single heat modalities currently employed.

One of the major uses for the above-described heating devices is for the treatment of hepatocellular carcinoma (HCC). Hepatic tumors are either primary or secondary (e.g., metastatic liver cancer (MLC)) and are a substantial medical problem both in the United States and worldwide. The worldwide annual mortality as a result of HCC is estimated to be approximately 1,000,000 persons.

Generally, chemotherapy and radiation therapy are ineffective for treatment of hepatic tumors and certain localized tumors where the above heating modalities are used. The gold standard for the treatment of liver tumors and many solid localized tumors is the surgical resection of the tumor. Unfortunately, less than 20% of patients of primary or secondary liver tumors are eligible for surgical resection due to tumor size. This is also the case where solid tumors have advanced in size, so that it may not be possible to remove the tumor from the organ without compromising the well being of the patient. Even with surgical resection, 5 year survival rates are less than 30%. The outlook is less favorable for patients with unresectable hepatic tumors. Thus, there is a major need for a more effective treatment option for both resectable and unresectable tumors.

Radio Frequency ablation for the treatment of liver cancer was first investigated in the early 1990s. Since that time RFA has quickly become one of the most frequently used minimally invasive treatments for HCC and MLC. There are numerous RFA devices commercially available worldwide to create the thermal energy that ablate the cancer cells. The three primary RFA devices utilized in the U.S. are those made by RITA Medical Systems, Mountain View, Calif.; Radio-therapeutics, Mountain View, Calif.; and Radionics, Burlington, Mass. The power sources of the three devices are very similar in usage, but the RITA Medical Systems and the Radio-therapeutics devices have an umbrella or "Christmas tree" configuration while the Radionics device uses a cool tip single, or multiple, needle design. The RITA Medical Systems device uses a temperature feedback control to terminate the treatment; whereas, the other two employ impedance feedback control. The clinical applications placing the RFA probes in the proximity of the tumor can be performed by open surgery or laproscopically, generally administered by a surgeon, or using a percutaneous treatment which is generally administered by interventional radiologists.

However, regardless of which RFA probes are used or which method of clinical application is used, the RFA treatments are best suited for smaller lesions less than 3 cm in diameter. Thus, all of the devices have similar limitations in the ability to effectively treat larger lesions, especially viable cancer cells in the margins of the lesion. The "margins" are defined by the area outside the solid tumor. The margins outside the boundary area of the tumor in most cases can be up to 2 cm in width. It is desirable to attempt to create tumor-free margins beyond the imaged tumor lesion of 1 cm or greater; however, RFA is often limited in its ability to produce such consistent margins especially for tumors with a maximum diameter greater than 3 cm. As a result, viable tumor cells are left within such margins (or the area between overlapping ablation zones) where tissue is heated above 40° C., but not to the necessary thermal ablation range (e.g., generally greater than 50° C.).

As a result, known RFA devices are only effective in limited areas that can be heated to high enough temperatures; generally greater than 50° C., and sometimes to temperatures greater than 80° C., in order to ablate the viable cancer. The high temperature makes it difficult to prevent damage to surrounding non-cancerous tissues. That is, it is difficult to heat the cancer cells at the margins to greater than 50° C. to kill the diseased tissue and at the same time avoid damaging the surrounding non-cancerous tissue.

High-energy Intensity Focused Ultrasound is another focused heating device. HIFU directs ultrasound to a focused region in order to achieve the temperature required to ablate diseased tissue in the targeted region. HIFU uses ultrasound thousands of times more powerful than that used for imaging. Several HIFU systems are clinically available (Ablatherm from EDAP-Technomed, Lyon, France and Sonablate from Focus Surgery, Indianapolis, Ind.), and several systems are under development in China, Europe, and the USA. Treatment applications have included localized prostate cancer, liver cancer, and benign breast and uterine tumors. With regard to the treatment of prostate tumors, these systems may be less invasive than surgery, cyroblation, or seed implants, but the use of HIFU has also been associated with adverse effects, such as incontinence, recto-urethral fistulas, edema, and chronic necrotic debris and infection. In addition, due to the time taken to treat using the pinpoint focus of HIFU and limitations on the size of the treatment zone, complete ablation and thus control of the tumor will be very difficult to achieve with these known systems. HIFU has also been used for other localized cancers; however, it has only achieved marginal success due to difficulty of use, limited size of ablation area, and difficulty of focusing and directing the energy to exactly where it is required.

Other technologies, such as lasers as developed by Indigo and Johnson & Johnson, transurethral incision of the prostate (TULIP), and visual laser ablation (VLAP), have similar limitations and clinical shortcomings to those of RFA. These shortcomings include the limited size of the effective targeted area and potential adverse effects caused by the high intensity heat. The inability to see in real time the amount of heat generated and the actual location of where the greatest amount of heat is generated can lead to significant cell death of the adjacent healthy cells. In addition, heat is distributed non-uniformly within the targeted treatment zone and does not extend effectively to the margins of the lesions or tumors.

Microwave ablation probes have been used to deliver heat to lesions and tumors, but this technology is invasive. This technology is very similar to RFA technologies. To some extent, MA may be limited by the fact that the regions around blood vessels can sometimes act as heat sinks; these heat sinks can result in cool spots that fail to achieve sufficiently high temperature to kill the lesion or tumor. Another potential limitation of MA is that it can take more time to heat a very confined area of lesion or tumor tissue.

Drug therapy is the standard of care (SOC) for the treatment of many cancerous and infectious diseases. The goal of drug therapy is to deliver an adequate dose of a drug to a specific site to be treated without damaging or killing normal cells. Cytotoxic drugs are generally delivered systemically and thus are neither site-specific, nor cell-specific. As a result, the delivery of cytotoxic drugs can damage normal cells and vital organs. To address this problem, several new drugs have been designed to specifically target cancerous cells by binding to tumor cell specific antigens. These drugs are typically very effective because they only kill specific tumor cells which have the targeted cell surface receptors. Furthermore, due to certain physical and physiological limitations, higher and more effective doses of anti-cancer agents are generally not achievable. However, for many localized lesions within organs such as the liver, prostate, lung, esophageal and breast, complete tumor control (including the tumor margins) has not been significantly improved, nor has there been a dramatic increase in survival rates.

With prostate cancer, for example, the goal is to provide an effective treatment to the diseased region within the gland, without causing major adverse events such as incontinence, sterility, pain, impotence or retrograde ejaculation. These adverse events are also a byproduct of surgery, external radiation and implant therapy, cryotherapy, and RFA. Even with thermotherapy, it can be difficult to heat a significant portion of the prostate gland while sparing healthy tissues therein as well as in the surrounding tissues (such as the urethral and rectal walls). Thus, cancer cells in the margins may not be effectively treated. The prostate, which is the most frequently diseased of all internal organs, not only is a site of cancer among older men, but also for benign prostatic hyperplasia (BPH) and acute prostatitis. Recent treatment of BPH includes transurethral microwave thermotherapy in which microwave energy is employed to elevate the temperature of tissue surrounding the prostatic urethra above about 45° C., thereby thermally damaging the tumorous prostate tissue. U.S. Pat. Nos. 5,330,518 and 5,843,144 describe methods of ablating prostate tumorous tissue by transurethral thermotherapy.

There remains a need to better treat diseased tissue to increase the survival rate of patients and decrease the adverse side effects of treatment. A long felt need in the art of cancer treatment exists to provide therapies that treat an entire tumor, including treatment at the margins without damaging normal non-diseased tissue. Methods solving this long felt need could include methods that achieve an increased concentration of a drug localized at the site of treatment. Therapies could be used not only for treatment of cancers, but also other localized disease states as well.

SUMMARY OF THE INVENTION

The present invention relates to an apparatus and a method for administering focused energy to a target site in a subject using either a single energy applicator or multiple energy applicators to supply heat prior to, concurrently with and/or after delivery of a liposome and/or a nanoparticle, for example a thermosensitive liposome or nanoparticle, and/or a thermo-activated drug, gene and/or viral vector. Embodiment of the invention relate to a multi-modality method of treatment using a localized, focused and/or regional heating apparatus, which supplies heat to a defined treatment area, for example an area of a patient's body. The apparatus is used to heat or pretreat a specific site, and to trigger the release of active agents from liposomes and/or activate thermo-activated drugs at the body site. The heating apparatus includes one or more variable and adjustable probes and one or more delivery ports to heat the specific treatment site and to activate liposomes or drugs to release an active agent at the specific treatment site. Each probe may optionally include one or more temperature sensors to permit the regulation of temperature at the specific treatment site and in the surrounding tissue. The use of the apparatus and method allow for the heat conditioning of a specific treatment site and the activation of thermosensitive liposomes and/or thermo-activated drugs at the specific treatment site, allowing for a more accurate treatment of diseased tissue without damaging healthy tissue.

Furthermore, the apparatus according to the invention addresses the shortcoming mentioned above in that the apparatus permits the user to see in real time the amount of heat generated at a specific location and the actual location where the high heat is generated; thus, the user can effectively target the heat and avoid significant cell death in surrounding tissue.

The method of the present invention includes the steps of determining the size and shape of a treatment area of diseased tissue, heating the treatment area to a desired temperature, using one or more temperature sensors to receive feedback about the temperature in the treatment area and in the surrounding healthy tissue, adjusting the heating of the treatment area to control the heating of the treatment area, and introducing thermosensitive liposomes and/or thermo-activated drugs into the treatment area, whereby the heat applied to the treatment area releases active agents from the liposomes and/or activates the drugs to allow for the treatment of the diseased tissue in the treatment area. The introduction of the heat is preferably accomplished by the use of one or more energy applicators, such as Radio Frequency Ablation, Microwave Ablation, Laser Ablation, Ultrasound Ablation, High Intensity Focused Ultrasound, and/or focused microwaves. The liposomes and/or drugs are introduced to the treatment area by intravenous (I.V.) or intra-arterial injection (where the active agents are released from the liposomes and/or the drugs are activated in the treatment area by the applied heat) or by direct intra-tumoral injection. Alternatively, the drugs can be administered systemically.

A further embodiment of the method according to the present invention is to pre-condition or condition the targeted tissue prior to the delivery of the thermosensitive liposomes and/or thermo-activated drugs. The step of introducing the heat initially enhances the release of active agents from liposomes, particularly thermosensitive liposomes, and/or activates thermo-activated drugs in the targeted tissue.

In addition, another embodiment of the inventive method includes the administration of heat to the site simultaneously with the delivery of liposomes and/or thermo-activated drugs to the targeted tissue. The heat can also be administered to the site post delivery of the liposomes or drugs to the targeted tissue.

The present method involves the use of dynamic heat control to optimize the spatial delivery of a rigid temperature to a targeted tissue within a narrow or limited temperature range (e.g., within about 2° C. to about 3° C. of a given temperature). In another embodiment, the method involves the use of dynamic heat control to allow the spatial delivery of a broad range of temperatures to a targeted tissue (e.g., over about a 0° C. to about 15° C. range or about a 0° C. to about 10° C. range). Exemplary temperature ranges to release active agents from thermosensitive liposomes and/or activate thermo-activated drugs include from approximately 40° C. to about 55° C. and from approximately 40° C. to about 50° C. That is, when a liposome or thermo-activated drug is employed, the liposome or drug may be designed to release active agents, or become activated, respectively, in the tissue and/or blood stream at temperatures ranging between about 40° C. to about 42° C., between about 39° C. to about 41° C., or any other 2° C. to 3° C. temperature range within the about 40° C. to about 55° C. range or from about 40° C. to about 50° C. Similarly, a broad range temperature release could be designed to release active agents from thermosensitive liposomes and activate thermo-activated drugs when the tissue is heated over about 40° C. to about 55° C. range.

An additional exemplary method within the scope of the invention involves the use and control of a static and/or steady state heating profile to optimize the spatial delivery of a rigid temperature release of active agents from thermosensitive liposome and/or thermo-activated drug in the targeted tissue. The temperature is designed to release active agents, or activate drugs, within a designated narrow temperature range (e.g. within about 2° C. to about 3° C. of a given temperature). The method can also be used with a static and/or steady state heating profile to optimize the administration of a broad temperature range to release active agents from thermosensitive liposomes and/or activate thermo-activated drugs in the targeted tissue. The broad range temperature release can be designed to release active agents over about a 0° C. to about 15° C. range or about a 0° C. to about 10° C. range. Exemplary temperature ranges include from about 40° C. to about 55° C. and from about 40° C. to about 50° C.

Embodiments of the method according to the invention include the administration of heat to the site prior to, simultaneous with, and/or after delivery of liposomes or thermo-activated drugs to the targeted tissue. In addition, this method could be used with either static or dynamic heat control, and with broad or limited temperature ranges, depending on the composition of the drug and the liposome membrane.

Furthermore, an exemplary method of the invention uses either a single heating profile or combinations of various heating profiles created by the various technologies which can be used either by controlling the dynamic heating profiles or the static and/or steady state profiles of each heating technology. This method can be used with selected release temperature ranges over about a 0° C. to about 15° C. range or about a 0° C. to about 10° C. range. An exemplary temperature range to release active agents from thermosensitive liposomes and to activate thermo-activated drugs is from about 40° C. to about 55° C. Another exemplary temperature range to release active agents from thermosensitive liposomes and to activate thermo-activated drugs is from about 40° C. to about 50° C. In addition, this method can be used with specifically designed release of active agents from liposomes and activation of drugs within a limited temperature range; i.e., about 1° C. to about 2° C. of a given temperature. Thus, any narrow tolerance within a given temperature range can be used to release the active agents and/or to activate the drugs in a targeted tissue.

Embodiments of the present method address the inability of currently-available methods to display in real time the amount of heat generated in a precise location. The above method can be combined with other technologies such as non-invasive approaches including, but not limited to, real time MRI, ultrasound, CT, laser, infrared, PET, and/or other imaging technologies to achieve the desired results. In addition, another embodiment of the method employs the use of microwave or RF radiometer technologies to achieve the desired results.

The apparatus of the present invention can include a catheter, at least one probe, a control unit, and conduits for transferring liquids and gases, for transferring energy, and for transferring temperature readings. There can be a plurality of probes, each including at least one of a temperature sensor, a fluid or gas port, and an energy emitter. In one embodiment, each probe includes a plurality of temperature sensors, fluid or gas ports, and energy emitters. Some embodiments may have probes that include energy emitters alone or energy emitters with temperature sensors and fluid ports or temperature sensors. The temperature sensors can be used to read the temperature in different sections of the treatment zone to allow for the heating of the treatment zone and to control the heating process to ensure that the treatment zone remains at the desired temperature and that the surrounding healthy tissue around the treatment zone does not become overly heated. The fluid and gas ports can be used for direct injection of a thermosensitive liposome and/or thermo-activated drug into the treatment zone. These ports may also be used to deliver cooling liquid or gas into the treatment zone. The energy emitters can deliver an energy source to the treatment zone that heats the diseased tissue in the treatment zone to the desired temperature. The desired temperature can be below the normal ablation temperature so that surrounding tissue is not damaged by the heating of the diseased tissue, but is sufficient to release active agents the liposomes and/or activate thermo-activated drugs introduced into the treatment zone. By using a lower heat level in combination with the liposomes or drugs, the apparatus of the invention can provide for the precise treatment of diseased tissue without significantly harming the surrounding healthy tissue. The design of the device allows for a user to fix and control the size and shape of a treatment zone, which allows for the more directed treatment of only the diseased tissue, and can kill the diseased tissue at the margins of the treatment area, while not damaging the surrounding healthy tissue.

BRIEF DESCRIPTION OF THE DRAWINGS

These and other features and advantages of the invention will be further understood from the following detailed description of the preferred embodiment with reference to the accompanying drawings in which.

DETAILED DESCRIPTION OF THE INVENTION

Figures 1, 1A:
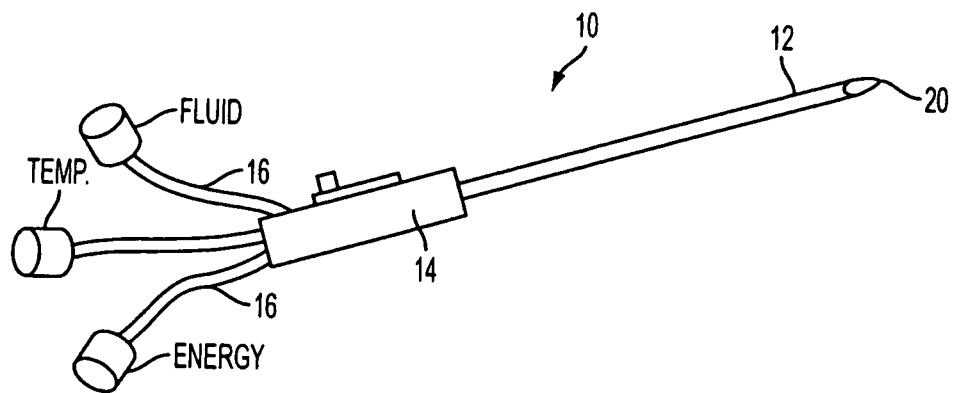
FIGS. 1A-1, 1A-2, and 1A-3 illustrate a variable extendable energy probe according to a first embodiment of the invention.

Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. All references cited herein are incorporated by reference as if each had been individually incorporated.

As used herein, "active compounds" or "active agents" include compounds such as organic molecules, proteins, enzymes, genes, viral vectors, etc. that have a desired biological effect. In particular the biological effect includes treating a disease condition such as cancer or tumors. Active compounds or active agents include compositions that may comprise more than one individual component to achieve the desired effect. Exemplary types of active agents include anesthetics, anti-histamines, anti-neoplastics, anti-ulceratives, anti-seizure agents, muscle relaxants, immunosuppressive agents, anti-infective agents, non-steroidal anti-inflammatory agents, imaging agents, nutritional agents, and mixtures thereof, for example. Exemplary anti-neoplastic agents include, but are not limited to, anthracyclines, such as doxorubicin and epirubicin; taxanes, such as taxol and taxotere; and platins, such as cis-platin, carboplatin and oxaliplatin.

As used herein, "liposomes and nanoparticles" are referred to collectively as "liposomes." Liposomes for use in the invention are generally heat sensitive and release encapsulated or associated agent(s) upon heating at temperatures of 70° C. or less. The liposomes useful with the invention can contain one or more active agents. Liposomes and nanoparticles can be selected to release active agents in temperatures of about 40° C. or higher, for example in the range of about 40° C. to about 50° C. or about 40° C. to about 55° C. Liposomes and nanoparticles include thermosensitive liposomes and nanoparticles. Exemplary thermosensitive liposomes are described in, for example, Needham, U.S. Pat. Nos. 6,200,598 and 6,726,925; Ogawa, U.S. Pat. No. 5,094,854 incorporated herein by reference. Thermosensitive liposomes and nanoparticles (collectively referred to herein as "thermosensitive liposomes") are those which release contents, for example an encapsulated or associated active agent, upon heating at a temperature of 45° C. or less. For example, thermosensitive liposomes include those that release an active agent in the range of about 39° C. to about 45° C., for example, about 40° C. to about 44° C.; about 40° C. to about 43° C.; about 39° C. to about 41° C. to about 42° C. "Thermo-activated drugs, genes and viral vectors" are referred to herein collectively as "thermo-activated drugs", and in some cases, simply as "drugs."

Thermo-activated drugs include any composition, for example a single molecule or a pharmaceutical composition composed of one or more active agents together with pharmaceutically acceptable recipients, which, upon heating to a target temperature, undergo a change to release an active compound or composition. Non-limiting examples of thermo-activated drugs include: compositions having active compounds encapsulated therein (including a liposome composition) that release the encapsulated active compound upon heating; compositions having an active compound bound thereto by, for example, ionically bonded, covalently bonded, or bonded through van deer Wails or other intermolecular interactions, which, upon heating, the bond breaks to release an active compound; and prodrugs or compositions containing prodrugs which, upon heating, undergo a chemical change to convert the prodrugs into an active agent. Thus, activation of thermo-activated drugs, includes any process in which an active agent is released to have a biological effect. In principle, thermosensitive liposomes are thermo-activated drugs that release an encapsulated active agent when heated. As used above "heated" means within a temperature range of about 39° C. or higher, for example in the range of about 40° C. to about 50° C.; about 40° C. to about 55° C.; about 40° C. to about 44° C.; about 40° C. to about 43° C.; about 39° C. to about 41° C.; about 40° C. to about 42° C.; or less than 45° C.

The present invention relates to a multi-modality method of treatment which employs a localized, focused and regional heating apparatus to treat and/or pretreat a specific body site so as to release active agents from liposomes, particularly thermosensitive liposomes, and/or to activate thermo-activated drugs at a specific body site.

The invention further relates to the use of ultra-sound energy to release active agents from liposomes and/or activate thermo-activated drugs. Thus, the method involves the use of one or more energy applicators designed to initiate the release of active agents at a specific treatment site. Heat energy may be used to precondition and/or condition a targeted treatment site to cause the localized release of active agents from the liposomes and/or the activation of thermo-activated drugs at the treatment site by establishing thermo-boundaries formed by the heat before, after and/or concurrently with the delivery of the liposomes and/or drugs. Similarly, ultrasound energy can be applied at a targeted treatment site to release active agents from liposomes either concurrently with or after delivery thereof. As a result, the invention can limit and/or increase the targeted treatment site and minimize the impact on normal cells.

In some embodiments, the present invention is directed to a device and a method for thermally treating tissue in both limited and expanded therapeutic zones by heating a target tissue prior to, simultaneous with, or after delivery of an active agent or drug to the desired treatment area. The targeting of heat to a specific treatment area in this manner enables the release of active agents from a liposome and/or the activation of thermo-activated drugs for the treatment of cancerous, precancerous, or benign lesions as well as infectious diseases.

In other exemplary embodiments, the present invention relates to an apparatus and method for administering focused energy to a targeted area in a subject using one or more energy applicator including, but not limited to, Radio Frequency Ablation, Microwave Ablation, Laser Ablation, Ultrasound Ablation, High Intensity Focused Ultrasound, and/or focused microwaves, to release active agents from liposomes and/or to activate thermo-activated drugs for the treatment of cancerous, precancerous, or benign lesions as well as infectious and non-infectious diseases. For example, the present invention relates to a treatment using a localized, focused and/or regional heating apparatus to pre-heat or heat a targeted area to release the active agents and/or activate the drugs.

The present method includes the administration of heat, or another type of energy such as ultrasound, to precondition or condition a target site (a defined area of diseased tissue in a patient's body) and release active agents from a liposome and/or activate thermo-activated drugs at the site. The size of the target area is determined by the probe and the energy type and magnitude employed. For example, when heat is used as the energy source it can penetrate the tissue of the targeted area over a period of time and the tissue temperature will gradually decrease from the center as it approaches the boundary of the targeted area. See, e.g., FIGS. 10-21. Thus, the invention allows a desired target area to be treated. As a result, the active agents and drugs will be released and absorbed within the targeted area. Therefore, because the invention can allow for heating at a predetermined size and boundaries of the treatment zone, it can limit collateral damage to normal tissue. In certain embodiments, the use of the invention to pre-condition and/or condition will also fix and limit the area of exposure of the active agents and/or drugs. Consequently, the invention demonstrates an increased ability to reduce tumor burden, especially for larger lesions and at the margins of the lesion, compared to the prior art. "Tumor burden" is defined as viable cancer cells within a particular volumetric area.

The step of applying energy to the target area may involve a single energy applicator or multiple energy applicators. The applied energy provides fixation and localization of the release of active agents from liposomes and/or the activation of thermo-activated drugs at the specific treatment site. Consequently, the invention can use lower temperatures than the prior art heating methods. The use of lower temperatures can help prevent damage to the surrounding healthy tissue, while at the same time permitting treatment of a targeted site with liposomes and/or thermo-activated drugs. It is also possible that the applied energy could be used to cool a target area to activate liposomes and drugs that are activated when exposed to temperatures cooler than the ambient temperature of a human being.

In order to increase the effective treatment field, as well as to verify and confirm the size of the treatment field, the present method can use adjustable temperature sensors and multiple point or individual sensors. The use of adjustable temperature sensors enables the heat to be limited to a desired distance from the heating probe. Thus, the adjustable temperature sensors of the present invention will also act as a safety control in the heating of the target site so that activation of drugs or release of active agents in normal healthy tissues is reduced. The ability to adjust and either expand or retract the heating probes of the invention enables one to customize the heat over a desired heating zone without the need to employ different fixed-sized heating probes for each desired heating zone. The clinical outcome is to provide and deliver a larger kill zone of the lesion or tumor (targeted site), which overcomes clinical limitations of known heat energy systems. One unique feature of this invention is that the user can predetermine the size and shape of the targeted area prior to, or concurrent with, the administration of liposomes and/or drugs.

The liposomes and/or thermo-activated drugs can be delivered by intravenous or intra-arterial injection or direct intra-tumoral injection to a targeted region or administered systemically. The instant method may employ focused heating devices including, but not limited to, Radio Frequency Ablation, Microwave Ablation, Laser Ablation, Ultrasound Ablation, High Intensity Focused Ultrasound, and focused microwaves as the energy source to trigger the release of active agents from thermosensitive liposomes and/or to activate thermo-activated drugs. However, in the case of RFA, the heating apparatus of the present invention may use single and/or multiple energy applicators to deliver thermosensitive liposomes and thermo-activated drugs to a specific treatment site. In addition, the applied heat energy of the present invention allows for the targeting and localization of the release of active agents from liposomes and/or the activation of thermo-activated drugs at a specific treatment site based on the unique thermo-boundaries formed by the use of the apparatus described herein.

Exemplary methods can use the apparatus to deliver only energy to the target area while using intravenous or intra-arterial injection of thermosensitive liposomes and/or thermo-activated drugs, rather than direct intra-tumoral injection of the liposomes and drugs. In an alternative embodiment, the method can use the apparatus to intra-tumorally inject liposomes and/or thermo-activated drugs into the target area while using a different source to apply energy to the region. Other embodiments of the invention use the device to preheat (i.e., precondition) the target area, followed by continued heating of the target area in combination with the introduction of liposomes containing active agents by direct injection into the target site through the device. The method may also be suitable for use with drugs that are effective at normal human body temperature, but increase in activity at a different temperature. Thus, unlike known ablative techniques, the instant invention may use temperatures that are significantly below the generally accepted therapeutic ablation temperatures of about 50° C.

The present method can heat the target area to a temperature sufficiently high enough to release drugs from liposomes and/or activate thermo-active drugs while also low enough to prevent damage to the surrounding healthy tissue. The heating range will depend upon the specific drug or liposome composition, but exemplary methods use a temperature less than about 55° C., for example less than about 50° C., or less than about 45° C.; or from about 40° C. to about 44° C.; from about 40° C. to about 43° C.; from about 39° C. to about 41° C.; or about 40° C. to about 42° C. from about 39° to about 41° C. about 40° to about 42° C. As discussed above, examples of thermosensitive liposome compositions are described in Needham, U.S. Pat. Nos. 6,200,598 and 6,726,925; and Ogawa, U.S. Pat. No. 5,094,854.

The use of energy focused heating devices including, but not limited to, Radio Frequency Ablation (RFA), Microwave Ablation (MA), Laser Ablation (LA), Ultrasound Ablation (UA), High Intensity Focused Ultrasound (HIFU), and focused microwaves (FM) achieve a minimally invasive approach when used in combination with liposomes and/or thermo-activated drugs. The present method fulfills the clinical need for optimizing the treatment of lesions and tumors by treating the core as well as the margins of the lesions and tumors.

Methods described herein optimize the treatment of the target tissue and address the shortcomings of current treatment technologies.

One embodiment of the method involves the delivery of heat to the site prior to the delivery of the thermosensitive liposomes and/or thermo-activated drugs to pre-condition or condition the targeted tissue. In another embodiment of the present method, the heat can be delivered to the site simultaneously with the delivery of the thermosensitive liposomes and/or thermo-activated drugs. In yet another embodiment of the method, the heat can be delivered to the site after delivery of the liposomes and the drugs.

The present method can employ a dynamic heat control to spatially deliver heat within a narrow temperature range to the targeted tissue. For example, the apparatus can be set to a provide temperature which releases active agents within about 2° C. to about 3° C. of a designated temperature. In other embodiments, the method can employ a dynamic heat control which results in the spatial delivery of heat over a broad temperature range. For example, the apparatus can be set to provide a temperature which triggers the release of active agents from a thermosensitive liposome and/or activate a thermo-activated drug over about a 0° C. to about 15° C. range or about a 0° C. to about 10° C. range. For example, one embodiment of the present method involves the use of a temperature range from about 40° C. to about 55° C. to release active agents from thermosensitive liposomes and/or activate thermo-activated drugs. Another example of the present method involves the use of a temperature range from about 40° C. to about 50° C. to release active agents from thermosensitive liposomes and/or activate thermo-activated drugs. When a narrow temperature release range is employed, a liposome may be designed to release the active agent and/or the drug may be designed to be activated in, a targeted tissue and/or the blood stream at temperatures ranging from about 40° C. to about 42° C., from about 39° C. to about 41° C., or any other 2° to 3° C. range. Similarly, the apparatus can be set to provide a temperature which releases active agents from thermosensitive liposomes and/or activates thermo-activated drugs when the tissue is heated over a temperature range of about 40° C. to about 55° C. or about 40° C. to about 50° C.

Another embodiment of the present method involves the use a static and/or steady state heating profile to spatially deliver heat to a targeted tissue to release active agents from liposomes and/or activate thermo-activated drugs over a narrow temperature range. The apparatus can be set to provide a temperature which releases the active agents and/or activates the drugs within about 2° to about 3° C. of a given temperature. In another embodiment, the method can use a static and/or steady state heating profile to release active agents from liposomes and/or activate thermo-activated drugs in a targeted tissue over a broad temperature range. The apparatus can be set to deliver a broad temperature range which releases active agents from the aforementioned liposomes and/or activates the aforementioned drugs over about a 0° C. to about 15° C. range or about a 0° C. to about 10° C. range. In one embodiment, the active agent is released from a thermosensitive liposome and/or the thermo-activated drug is activated over a temperature range of about 40° C. to about 55° C. or a temperature range of about 40° C. to about 50° C.

Thus, according to the method of the invention, the heat can be delivered to a targeted site prior to, simultaneous with, and/or after the administration of the thermosensitive liposomes and/or thermo-activated drugs, in order to pre-condition or condition the site and/or target the liposomes and drugs therein. In addition, this method can be used with either static or dynamic heat control to deliver either broad or a limited temperature range depending on the liposomes and/or drugs employed.

Furthermore, the method of this invention allows for the optimized treatment of targeted tissue. The method uses either an independent heating profile or combinations of the various heating profiles created by the various technologies. In addition, the method can be optimized for use over broad temperature ranges specifically designed to release active agents from liposomes and/or to activate thermo-activated drugs over about a 0° C. to about 15° C. range. Exemplary temperature ranges include from about 40° C. to about 55° C. and from about 40° C. to about 50° C. In addition, the method can be further optimized for use with a rigid temperature range specifically designed to release active agents and/or activate drugs within about 2-3° C. of a given temperature. Thus, the range of temperatures depends on whether a rigid temperature release or a broad temperature release is desired. A temperature range to release active agents from liposomes and/or activate thermo-activated drugs in a targeted tissue can be from about 40° C. to about 55° C. or from about 40° C. to about 50° C.

An exemplary feature of the inventive heating apparatus in the both single or multiple energy applicators is to provide one or more unique delivery ports to deliver liposomes and/or thermo-activated drugs to a specific treatment site thereby enabling the heating apparatus to effectively operate at a lower temperature. As explained above, the applied heat energy is used for the targeting and localization of both the release of active agents from the liposomes and/or the activation of the drugs at a specific treatment site based upon the unique thermo-boundaries formed by pretreatment heating or concurrent heating with the delivery of the drugs and/or the liposomes. In order to increase the effective treatment field as well as to verify and confirm the size and shape of the treatment field, both adjustable temperature sensors and multiple point or independent sensors may be disposed on an appendage(s) of the heating device. The ability to deploy adjustable temperature sensors will allow heating to be limited to a desired distance from the heating probe. As a result, the present invention can be used as a single modality, which preheats (or preconditions) or concurrently heats a desired area while the thermosensitive liposomes and/or thermo-activated drugs are separately administered by intravenous (I.V.) or intra-arterial injection and/or direct intra-tumoral injection by another device.

According to an embodiment of the invention, a preheating or preconditioning period of the targeted treatment zone may be performed by starting the heating by the energy emitting device for a period of approximately up to 10 minutes prior to the administration of the liposomes and/or drugs. Heat can also be administered at the same time as the liposomes and/or drugs. In addition, a cool down period may be used to target the liposomes and/or drugs in a treatment zone. This may be accomplished by cooled air, gas, fluid or other lower temperature medium inserted via the fluid ports that could be used to also dispense the liposomes and/or drugs to the targeted area. For example, a movable energy-emitting source (e.g., microwave antenna) having a variable length may have multiple accesses or openings along its variable length so that a liquid or gas drug, gene, or viral vector can exit the ports at different locations depending on the size and shape of desired treatment zone.

In the same manner, a temperature sensor could also be disposed along a variable length of a probe extending from the energy emitting device and/or multi-temperature sensors may be disposed along the length to allow for a better thermo mapping model. An exemplary embodiment could use one feature, a combination of any two, and/or a combination of all three: the antenna or energy emitter, liquid/gas ports, or temperature probes. These probes can also have radio or sonar markings so that devices, such as X-ray, ultrasound, MRI or other imaging technologies, can verify the physical placement of the energy emitting device of the present invention. In the same manner, one would be able to also view or treat the targeted treatment field if the probes have radio or sonar markings. Thus, the present invention can work together with either individual multi-channel array emitters or single emitters opening up into multiple array probes for the different energy modalities; e.g., Radio Frequency Ablation, Microwave Ablation, Laser Ablation, Ultrasound Ablation, High Intensity Focused Ultrasound, and focused microwaves.

The temperature sensors that can be used to control the size of the preconditioned or conditioned treatment zone may be either invasive, minimally invasive and non-invasive. For the invasive or minimally invasive technologies, use of thermostats, thermocouples, and/or fiber optics can be used. Another approach is the use of non-invasive temperature monitoring and control approaches such as, ultrasound, microwave, infrared, laser, CT, and, Magnetic Resonance Imaging (MRI).

A method using heat creates a targeted and pre-conditioned treatment zone. The delivery of the heat can be delivered to the targeted site pre-delivery, simultaneously with delivery, and/or after delivery of thermosensitive liposomes and/or thermo-activated drugs. The method according to this invention is to target the thermosensitive liposomes and/or thermo-activated drugs to the tissue to be treated.

Therefore, this invention improves upon the ability to address the limitations of heat alone modalities of the desired targeted treatment area. This invention uniquely uses heat as a precondition, conditioning and a fixation method that is controllable to a desired targeted treatment area. As a result, the present invention overcomes the shortcomings of known ablation techniques and addresses the limitations of thermosensitive liposomes, SOC drugs, and thermo-activated drugs by targeting a specific treatment site, delivering thermosensitive liposomes and/or thermo-activated drugs to the specific treatment site, activating the liposomes and/or the drugs in the preconditioned targeted area and enhancing the effectiveness of the limited, standard delivery. Due to the preconditioning of the target area by using heat generated by the energy-emitting device, this invention has the ability to predetermine the size of the targeted treatment area and/or to increase the effective treatment zone achieved with heat alone techniques. Moreover, the combination of pre-conditioning using heat and delivery of liposomes and/or drugs effectively can treat a larger targeted area with lower heating temperatures. Thus, the present invention enhances the targeted delivery and activation of the thermosensitive liposomes and/or thermo-activated drugs and SOC drugs, and also increases the targeted treatment zone.

Additionally, the present invention allows for control of the size of the heating zone by varying the temperature of the probe or the time at which the probe is heated to the desired temperature. Assuming a probe temperature of about 28-30° C. outside the target tissue, the use of a 90° C. probe for about two minutes can produce a 75° C. boundary extending approximately 2 mm beyond the probe. Probe temperatures can be varied to be, for example, about 45° C., about 50° C., about 60° C., about 70° C. or about 80° C. By varying probe temperature, a one minute heating internal can provide a 40° C. isotherm that can extend from the probe by from about 4 to about 14 mm, for example about 4.5 mm, about 7.4 mm, about 9.9 mm, about 10 mm or about 13.2 mm. Under similar conditions 50° C. isotherm can extend from 0 to about 7 mm from the probe, for example about 0 mm, about 3.6 mm, about 4.8 mm or about 6.9 mm.

Figures 1, 1A, 2:
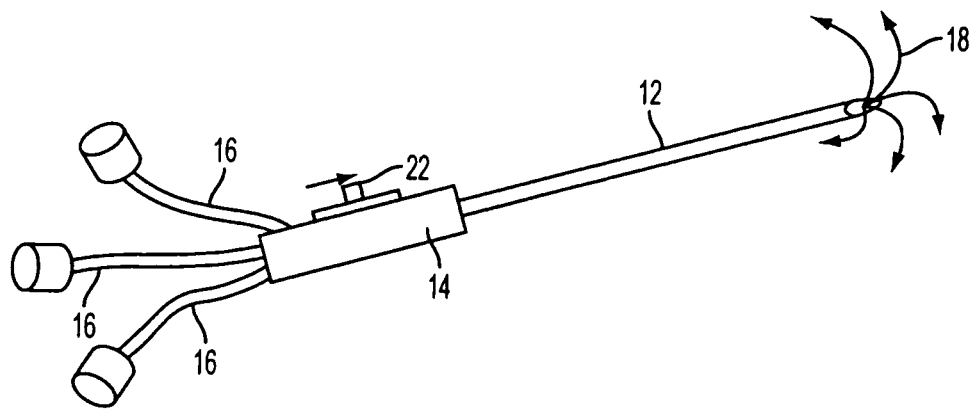
Figures 1, 1A, 2, 3:
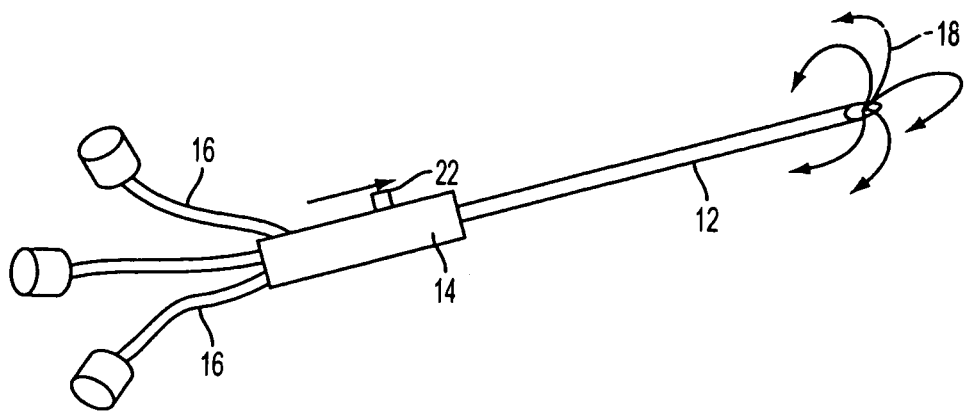

FIGS. 1A-1, 1A-2, and 1A-3 depict a preferred embodiment of the variable and adjustable probe device 10 used to treat diseased tissue. The device 10 includes a main catheter 12, which houses one or more probes 18. The lengths of the probes 18 are adjustable and variable. The catheter 12 is used to position the catheter port 20 at the catheter's tip into the general vicinity of a patient's diseased tissue (the treatment site), and the probes 18 are then extended out of the catheter port 20 to treat the diseased tissue. The catheter end that is not positioned within a patient's body is attached to a control unit 14, which allows for the control of the extension of the probes by the activation of switch 22. FIG. 1A-1 shows the probes 18 in a retracted position that allows for the catheter to be easily positioned within the patient's body. FIG. 1A-2 shows the probes 18 in a partially extended position caused by the partial activation of switch 22. FIG. 1A-3 shows the probes 18 in a fully extended position caused by the full activation of switch 22. The switch 22 may be any type of switch now known or later developed, including an electronic push button switch or a mechanical slide switch. The control unit 14 may include a plurality of switches 22 which each independently control one or more of the probes 18, which would allow for a user of the device 10 to create a variety of differently shaped treatment zones. The control unit 14 is connected to conduits 16 for transferring energy, fluid, and temperature information. To introduce a liposome and/or nanoparticle and/or a thermo-activated drug through the device 10 directly to specific defined treatment area of diseased tissue in the patient's body, one would introduce the liposome or drug through the fluid conduit 16. The fluid conduit 16 may also be used to introduce cooled air, gas, fluid or other lower temperature medium into the treatment area. One or more forms of energy are delivered to the treatment area through the energy conduit 16. Temperature readings from the treatment area are received through the temperature conduit 16. The control unit 14 may control the introduction of matter or energy into the patient's body.

Figure 1B:
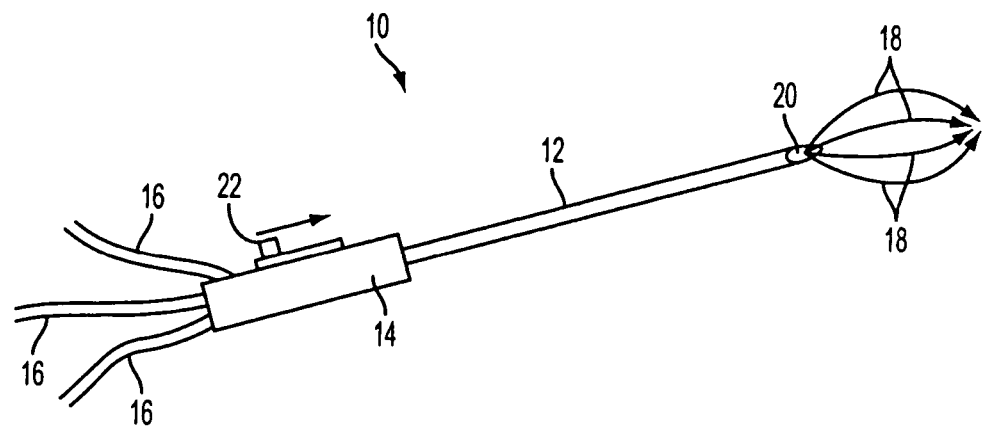
FIGS. 1B and 1C show another embodiment of a variable extendable energy probe according to the invention.
Figure 1C:
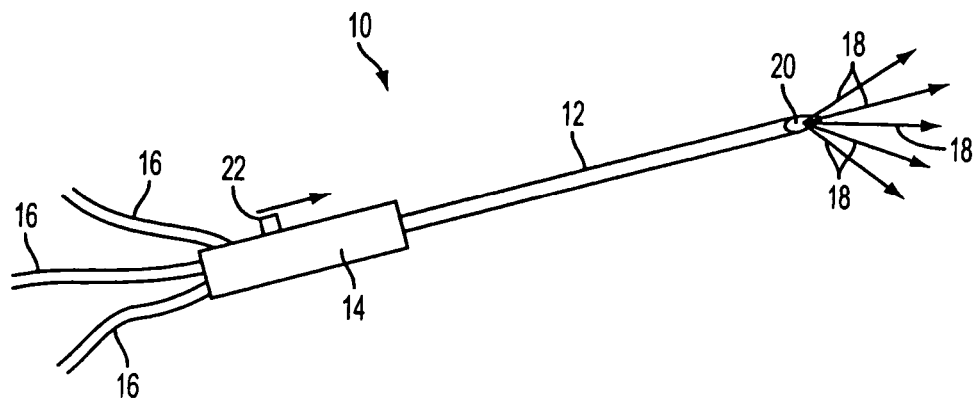

FIGS. 1A-2 and 1A-3 further show embodiments in which the probes 18 extend in a fish hook-like manner where the various probes twist back once they are extended out from the catheter port 20. The probes are formed such that they automatically come out in a fish hook-like array (J-shaped) once they are extended out of the catheter 12. The probes 18 of FIGS. 1A-1 through 1A-3 are variable extendable energy emitter. Depending upon the area to be treated, the probes 18 may be extended part way (FIG. 1A-2) or all the way out of the catheter port (FIG. 1A-3). FIG. 1B shows a second embodiment where the probes 18 form a bulging array (oval shaped) where the probes 18 exit the catheter port 20, at first diverging and then converging. FIG. 1C shows a third embodiment where the probes 18 form a linear array of probes diverging from a single point (the catheter port 20) in a linear fashion. These different embodiments of the probes 18 may be used to treat differently shaped and/or positioned treatment zones. The device 10 may be further designed to allow for the operator of the device 10 to select for the type of the probe array, as well as to select the degree of curvature of each probe by the use of the control unit 14. The device 10 may also allow for individual control of how each probe moves out of the catheter port 20, allowing for each individual probe 18 to be controlled for how far it is extended out of the catheter port 20, as well as for how each probe 18 curves.

Figure 2A:
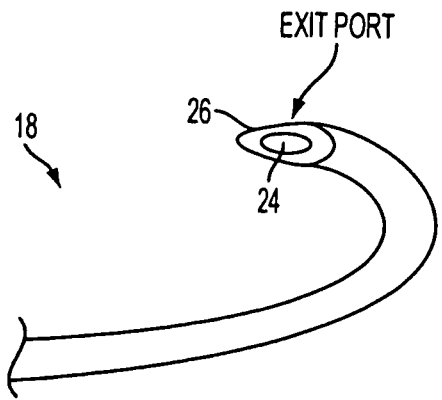
FIGS. 2A, 2B, and 2C are enlarged partial views of the extended probe showing a gas/drug/gene delivery exit port at the end of an extended probe.
Figure 2B:
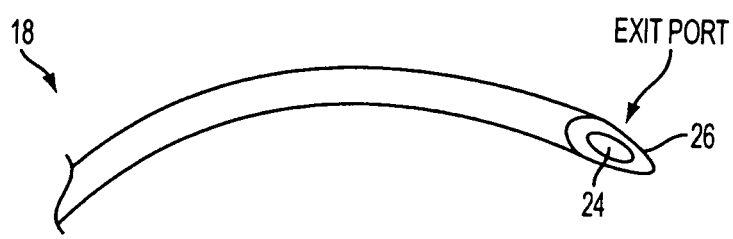
Figure 2C:
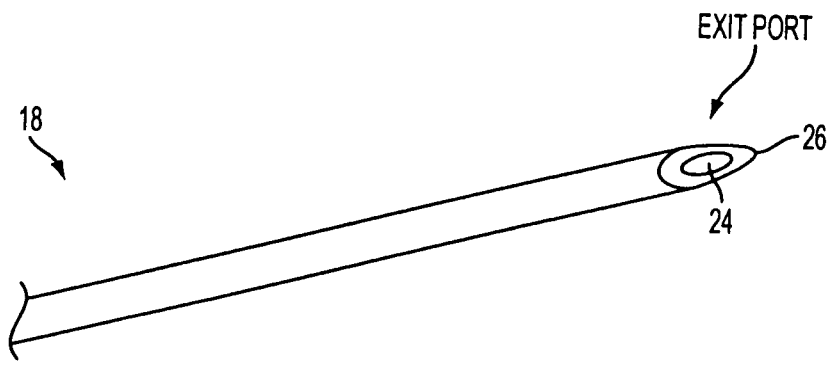
Figure 3A:
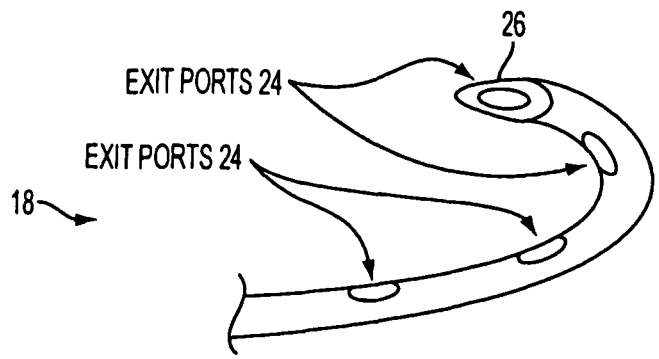
FIGS. 3A, 3B, and 3C show multiple delivery ports within one probe of an extended probe.
Figure 3B:
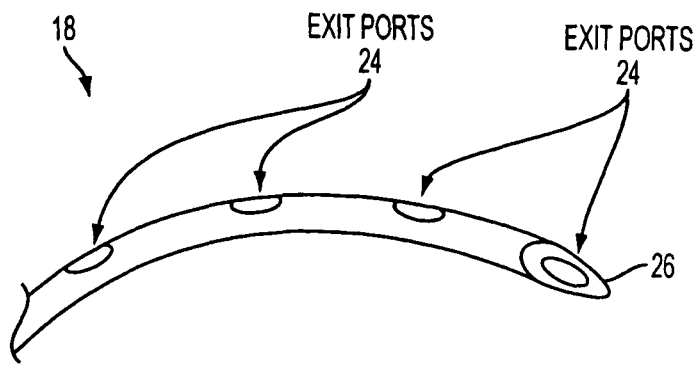
Figure 3C:
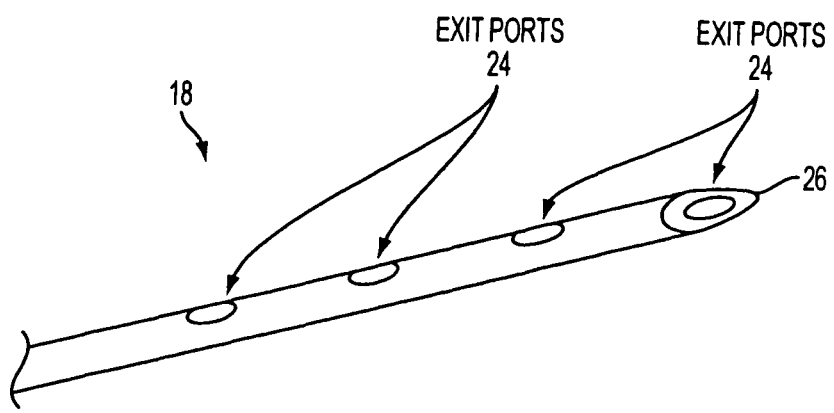

FIGS. 2A, 2B, and 2C show enlarged partial views of the extended probe 18 showing a gas/liposome/drug delivery exit port at the end of an extended probe. These three figures show the probe in the different embodiments of probe arrays as discussed above. Each probe in this embodiment is provided with a single fluid port 24 at the tip 26 of the probe 18 for introducing a liposome or drug to the treatment area. FIGS. 3A, 3B, and 3C show a second embodiment for providing probes 18 with fluid ports 24. Again, each of these figures show the probe in the different embodiments of probe arrays, as discussed above. Each probe in this embodiment includes multiple fluid ports 24 along the sides of the probe 18 as well as at the tip 26 of the probe 18. These fluid ports are in fluid connection with the fluid conduit 16 as shown in FIGS. 1A-1, 1A-2, and 1A-3, so that liposomes, drugs, or other fluid or gaseous media may be introduced into the treatment area of a patient's body through the device.

Figure 4A:
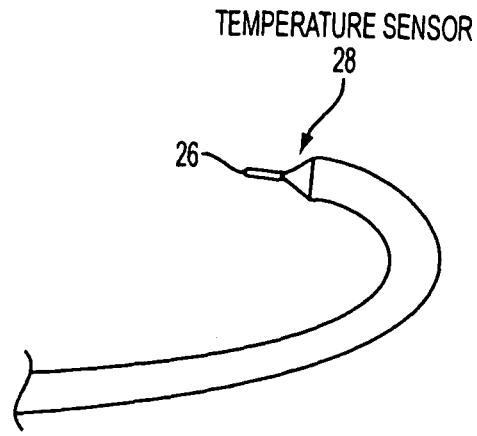
FIGS. 4A, 4B, and 4C are enlarged partial views of the extended probe showing a variable temperature sensor at the end of an extended probe.
Figure 4B:
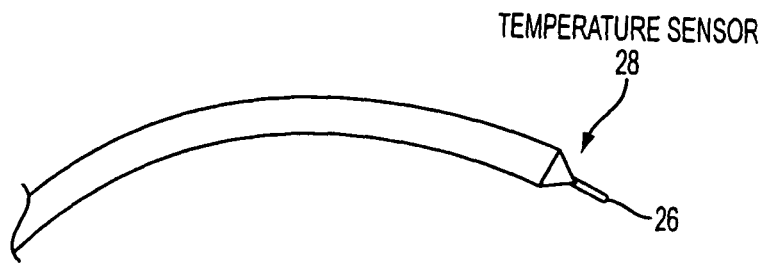
Figure 4C:
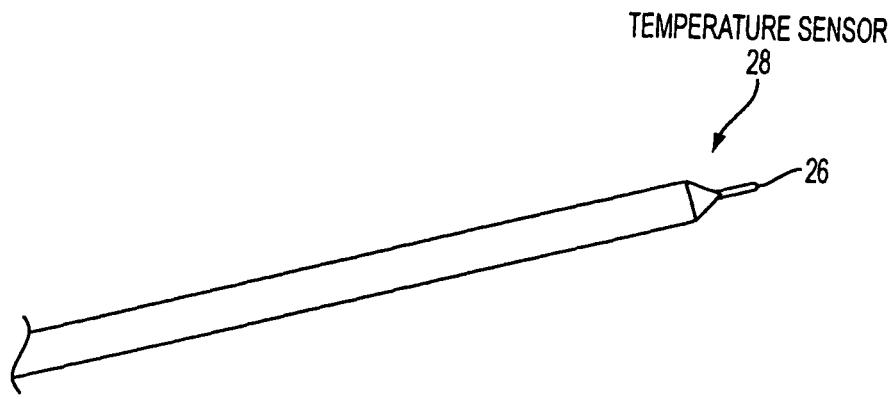
Figure 5A:
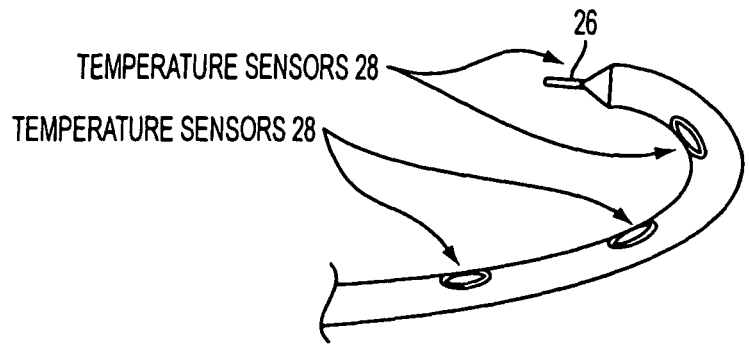
FIGS. 5A, 5B, and 5C are enlarged partial views of the extended probe showing multiple temperature multiple sensors disposed on an extended probe.
Figure 5B:
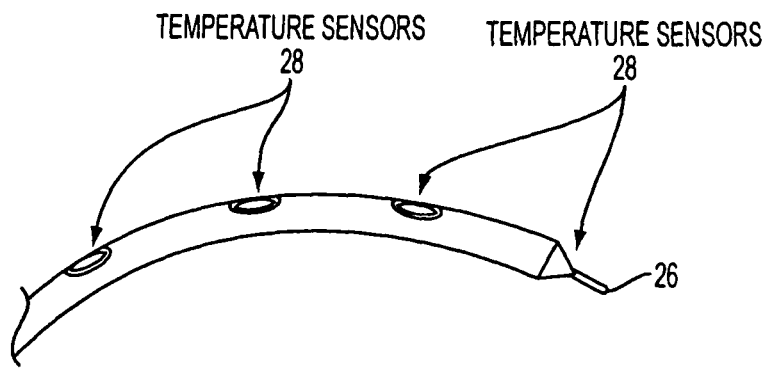
Figure 5C:
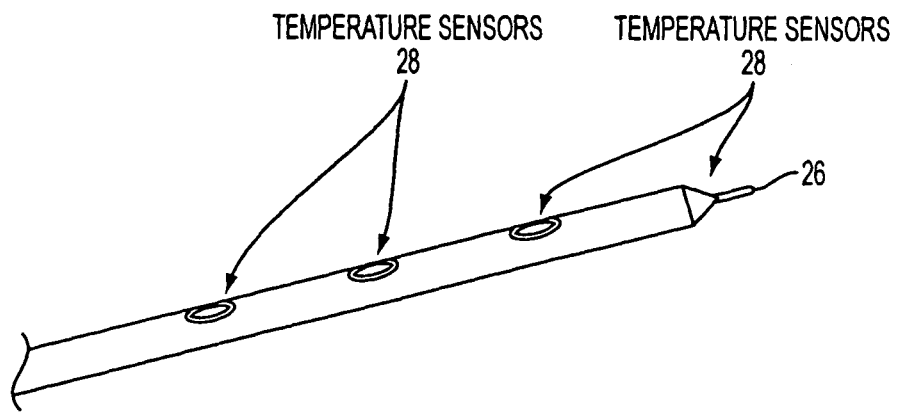

FIGS. 4A, 4B, 4C, 5A, 5B, and 5C show enlarged partial views of the extended probe 18 showing different embodiments having temperature sensors. FIGS. 4A, 4B, and 4C include a single temperature sensor 28 at the tip 26 of the probe 18. FIGS. 5A, 5B, and 5C include multiple temperature sensors 28 along the length of each probe 18 as well as at the tip 26 of each probe 18. These temperature sensors relay temperature reading information back through the temperature information conduit 16 so that the temperature information about the treatment location can be evaluated by a user of the device 10. The temperature information could also be analyzed by a device in the control unit 14 and displayed on the control unit 14. This information is used to adjust the amount and distribution of heat energy delivered to the treatment area so that the user of the device may ensure that only diseased tissue is treated while preventing damage to healthy tissue surrounding the treatment area.

Figure 6A:
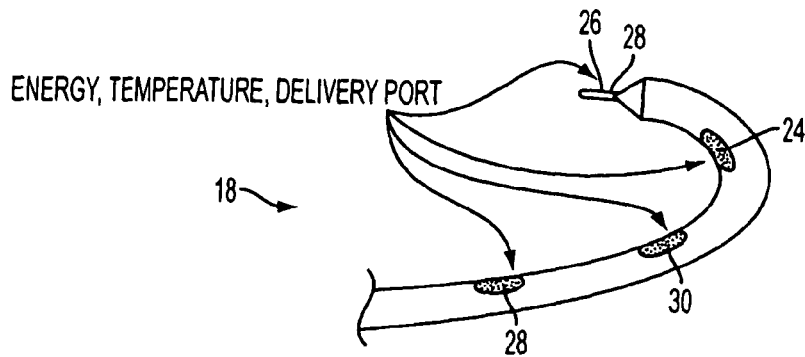
FIGS. 6A, 6B, and 6C are enlarged partial views of an extended probe with the multiple combinations of energy emitter, temperature sensor and delivery port disposed on an extended probe.
Figure 6B:
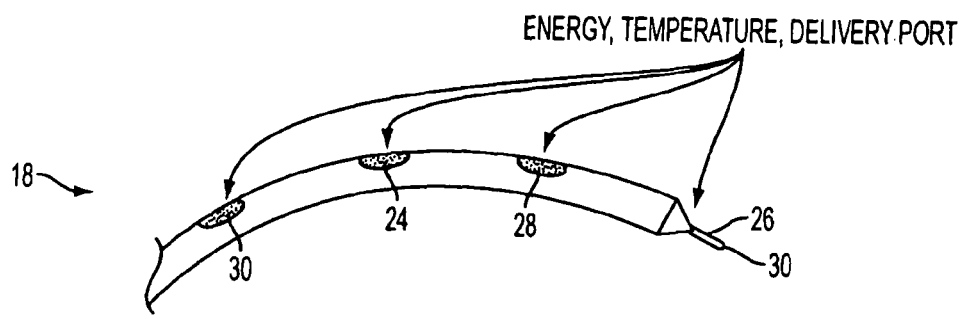
Figure 6C:
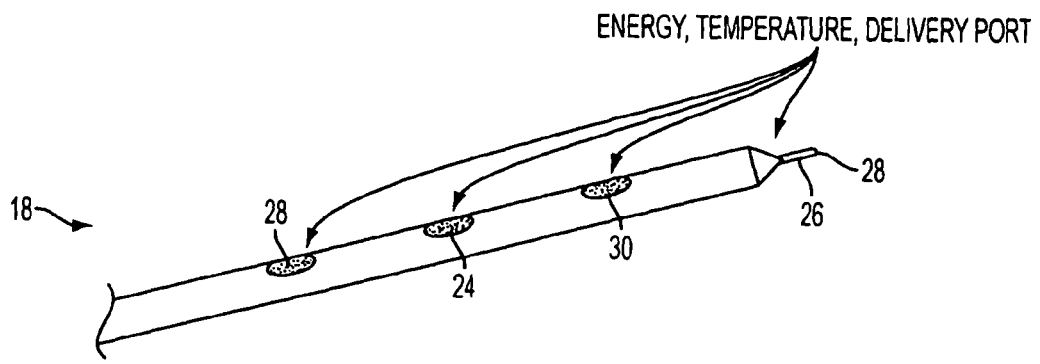

FIGS. 6A, 6B, and 6C show enlarged partial views of the extended probe 18 showing different embodiments having combinations of fluid delivery ports 24, temperature sensors 28, and energy delivery ports (energy emitters) 30. In this preferred embodiment, each probe has multiple temperature sensors 28, fluid delivery ports 24, and/or energy delivery ports (energy emitters) 30. With each probe having each of these types of sensors or ports would allow for the optimal level of treatment and control of the treatment of diseased tissue. The multiple energy ports (energy emitters) deliver heating energy to the diseased tissue so that the diseased tissue is preconditioned prior to the delivery of a liposome or thermo-activated drug and to heat the treatment area during and/or after delivery of liposomes and/or thermo-activated drugs to activate the liposomes and/or the drugs. The heating devices delivers energy in the form of Radio Frequency Ablation, Microwave Ablation, Laser Ablation, Ultrasound Ablation, High Intensity Focused Ultrasound, focused microwaves, or any other type of energy source as the minimally invasive or non-invasive energy. The device could also use these energy sources in combination. This heat is delivered to the treatment area through the energy ports (energy emitters) 30, through the probes 18 (which each travel through the catheter 12) through the control unit 14, through the energy conduit 16 from an initial energy emitting device delivering one or more of the above listed types of energy. Multiple energy conduits 16 would preferably be used if the device uses multiple types of energy forms to heat the treatment zone. The entire body of the probes 18 themselves may constitute an energy emitter 30, depending upon the type of energy delivery device used, but the energy emitters might also constitute ports for the delivery of energy prongs into the desired area of a patients body or for the transmission of energy waves to the desired area of a patient's body.

During the applications phase, a physical pulsing (turning on and off the energy source) may be used in the physical and mechanical caused by cell agitation to also aid in the activation and or release and absorption of the material applied to a patient via an intravenous or injection method. This application phase can also aid in the mechanical fixation of the liposomes and/or drugs and/or gene therapy compounds to the targeted protein and/or DNA tissue. It is noted that this mechanical method of fixation may cause the binding of the liposomes and/or drugs and/or gene therapy compound disposed in the coated balloon to the protein and/or DNA. The resultant binding of the liposome, drug or gene therapy compound to the targeted protein and/or DNA is a major new innovation to ensure that the desired compound is effectively fixated or delivered to the targeted tissue.

Figure 7A:
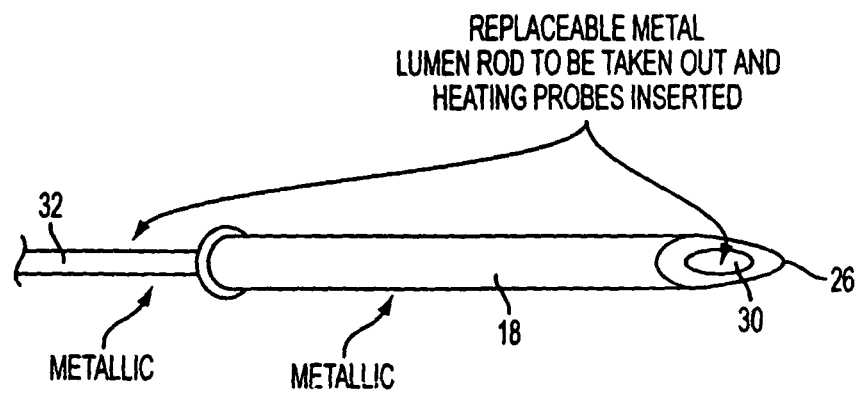
FIGS. 7A and 7B illustrate a single metal introducer of heat/temperature sensor/delivery ports in another embodiment of an extended probe of the variable extended probe device of FIG. 1.
Figure 7B:
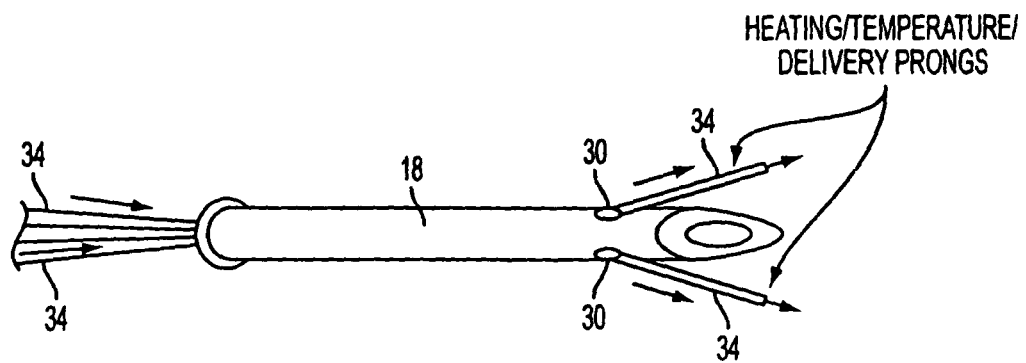

FIGS. 7A and 7B depict a further embodiment of an energy delivering probe 18 with a single metallic introducer energy delivery probe. In the embodiment depicted in 7A, a metallic rod 32 in inserted within the metallic energy delivery probe 18. The metallic rod 32 is removed once the probe 18 is adequately positioned in the treatment area of the patient's body and heating prongs 34 are inserted through the energy conduit 16 and through the energy delivery probe 18. FIG. 7B depicts the insertion of the heating prongs 34 into the energy delivery probe 18. In the embodiment of 7A, these prongs would exit the energy port 30 at the tip of the energy delivery probe 18. In the embodiment of 7B, these prongs exit the energy ports 32 along the side of the energy delivery probe 18.

Figure 8A:
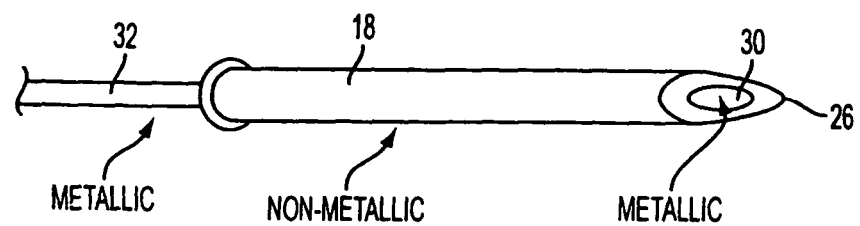
FIGS. 8A and 8B illustrate a single non-metallic introducer heat/temperature sensor/delivery ports in another embodiment of an extended probe of the variable extended probe device of FIG. 1.
Figure 8B:
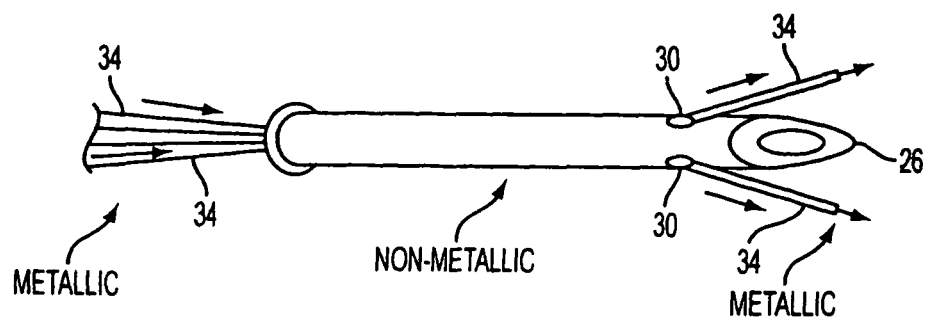

FIGS. 8A and 8B depict a further embodiment of an energy delivering probe 18 with a single non-metallic introducer energy delivery probe. In the embodiment depicted in 8A, a metallic rod 32 is inserted within the non-metallic energy delivery probe 18. The metallic rod 32 is removed once the probe 18 is adequately positioned in the treatment area of the patient's body and heating prongs 34 are inserted through the energy conduit 16 and through the energy delivery probe 18. FIG. 8B depicts the insertion of the heating prongs 34 into the energy delivery probe 18. In the embodiment of 8A, these prongs would exit the energy port 30 at the tip of the energy delivery probe 18. In the embodiment of 8B, these prongs exit the energy ports 30 along the side of the energy delivery probe 18. The heating prongs 34 of FIGS. 7B and 8B may also include temperature sensors.

Figure 9A:
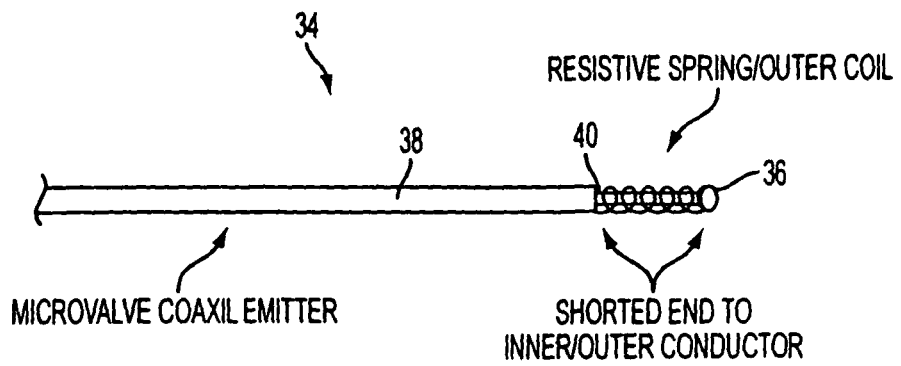
FIGS. 9A-9D show a unique microwave/resistive spring loaded short circuit antenna design that may be used in the probes of FIGS. 1-8.
Figure 9B:
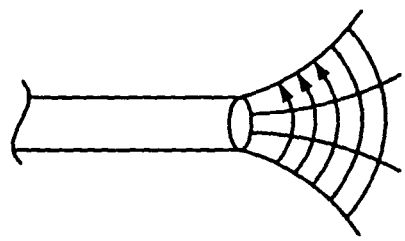
Figure 9C:
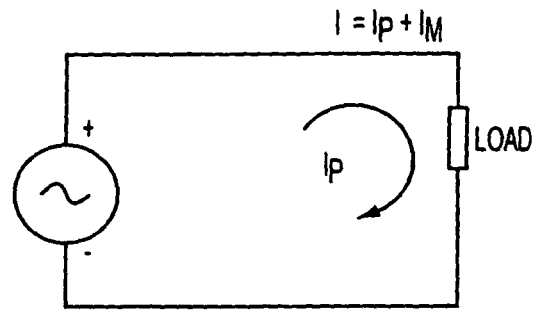
Figure 9D:
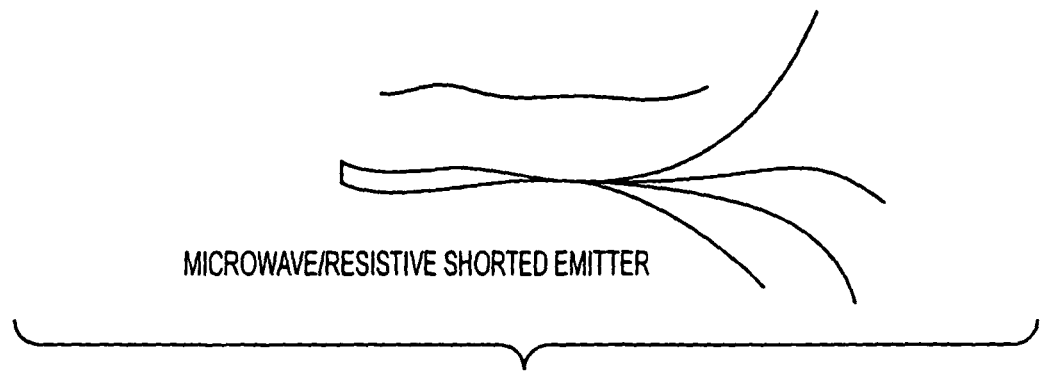

FIG. 9A depicts a unique microwave/resistive spring loaded short circuit antenna design that may be used as a heating prong 34. This improved heating prong, is provided with a resistive spring outer coil 40, and inner conductor 36, and an outer conductor 38. This unique arrangement when provided as the load in the circuit as shown in FIG. 9C provides a microwave-resistive shorted emitter as shown in FIG. 9D. This is an improved microwave emission over the prior art microwave emitter wave as shown in FIG. 9B. It not only heats with microwaves but the resistive spring load short delivers a direct current (DC). This new design overcomes the limitations of DC and MA technologies.

Figure 10A:
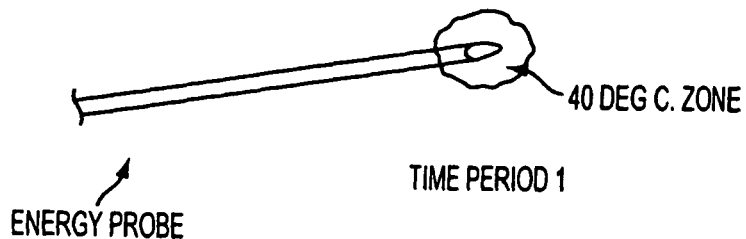
FIGS. 10A-10C illustrate the dynamic control of heat for the release of active agents from thermosensitive liposomes and/or the activation of thermo-activated drugs.
Figure 10B:
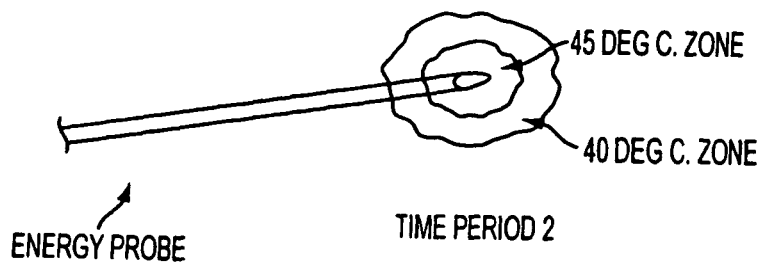
Figure 10C:
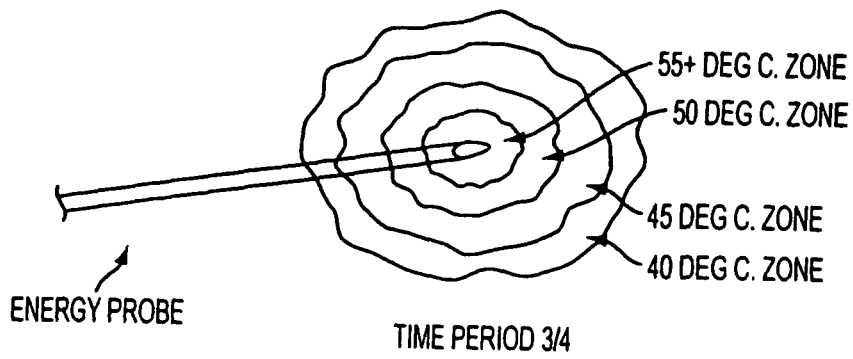

As illustrated in the four time periods shown in FIGS. 10A-10C, an energy probe 10' is inserted in a bodily conduit and serves to heat tissue adjacent to the bodily conduit. Initially, when the energy probe 10' begins warming up the surrounding tissue, an approximately 40° C. zone radiates from the energy probe during time period 1. During a second time period, two heating ringed areas exist. One is the 40° C. zone, which has moved further from the energy probe 10' and the other is a 45° C. zone that is within the 40° C. zone surrounding the energy probe 10'. Over time periods 1-4, dynamic temperature profiles move out away from the energy probe 10' so that the highest temperature is the ringed area adjacent energy probe and the temperature decreases in temperature as the ringed areas move away from the energy probe 10'. As shown in FIG. 10C, during time periods 3/4, the energy probe 10' heat the surrounding tissue in at least four different ringed temperature areas. The ringed area closest to the energy probe 10' may be an approximately 55° C. zone and the temperature zones of the ringed areas decrease as they move away from the energy probe 10' so that an approximately 50° C. zone surrounds the innermost ringed area and an approximately 45° C. zone surrounds the approximately 50° C. zone. As the time periods illustrate, the initial temperature of approximately 40° C. continues to move away from the energy probe 10' while new temperature zoned areas are created inside the outer 40° C. zone.

It is with this dynamic temperature profile that a range of temperature release of active agents from liposomes and/or the activation of thermo-activated drugs occurs in the 40° C. zone for each time period. That is, the thermosensitive liposomes and/or thermo-activated drugs may be designed so that the active agents are released and/or the drugs are activated in the 40° C. zone. As the 40° C. zone moves away from the energy probe 10', the liposomes and/or thermo-activated drugs that were injected prior to or during the heating would be activated at each 40° C. zone shown in each time period. This dynamic temperature profile determines when the active agents are released from the thermosensitive liposomes and the drugs are activated or fixed.

Figure 11:
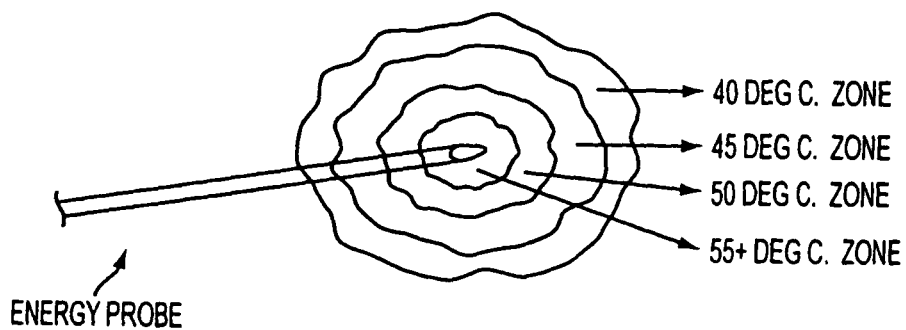
FIG. 11 illustrates the static and/or steady state heating profile for the release of active agents from thermosensitive liposomes and/or the activation of thermo-activated drugs.

FIG. 11 illustrates a static and/or steady state heating profile with rigid temperature formulation release of active agents from liposomes and/or activation of thermo-activated drugs. Basically, FIG. 11 shows an energy probe 10' and how the tissue surrounding the probe is heated in a ringed area after the probe has been heated for a sufficient time period to reach a static or steady state temperature. This is similar to time period 3/4 of FIG. 10C where the highest temperature ringed area zone is the closest to the energy probe 10' and the temperature of the ringed areas decrease as they move away from the probe. The static or steady state heating profile is used to release active agents from thermosensitive liposomes and/or activate thermo-activated drugs in the outer temperature zone (approximately 40° C.) in order to effectively treat the margins of a tumor where the effects of thermotherapy may be limited. That is, the combination of release of active agents and the activation of drugs with heat will improve the effectiveness of heat in killing the margins of a tumor.

Figure 12:
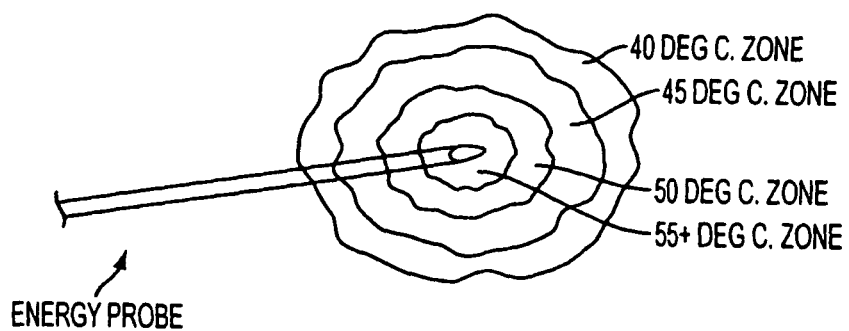
FIG. 12 illustrates the dynamic and/or static and/or steady state heating profile for the release of active agents from thermosensitive liposomes and/or the activation of thermo-activated drugs.

FIG. 12 illustrates a dynamic and/or static and/or steady state heating profile with broad temperature formulation release of active agents from liposomes and/or activation of thermo-activated drugs. During a dynamic and/or static and/or steady state heating profile the release of active agents and the activation of drugs is designed to occur over a broader temperature range of about a 0° C. to about 15° C. That is, the broad temperature range within which the active agents are released from thermosensitive liposomes and/or thermo-activated drugs are activated may range from about 40° C. to about 55° C., or a smaller range of about 40° C. to about 45° C.

The invention is effective for the treatment of cancer but may also be used to treat non-cancerous afflictions. The invention also encompasses the treatment of other sites, local and regional, besides the above mentioned prostate gland. The method may be used to treat cancerous, non-cancerous, and precancerous lesions as well as infectious diseases.

An exemplary use of the present method is for the treatment of esophageal cancer (EC). The incidence of esophageal cancer is increasing and currently represents 1% of cancers diagnosed annually in the U.S. (American Cancer Society, 2004; see www.acs.org) Globally, it ranks fifth in mortality rate among tumor types. (WHO, 2004; see www.who.org) Within the U.S., there are approximately 15,000 new cases of esophageal cancer diagnosed annually and 14,000 associated deaths, 4% of all cancer related deaths. (American Cancer Society, 2004) The 5 year survival of localized disease is 29% and across all stages of EC the 5 year survival is only 14%. The primary treatment for esophageal cancer is surgery in conjunction with radiotherapy and/or chemotherapy. However, EC is rarely curable.

There are two basic types of esophageal cancer, squalors cell carcinoma and Aden carcinoma. Over the last thirty years the incidence of the latter has increased substantially to become the most prevalent in the U.S. Demister SR, "Adenocarcenoma of the esophagus: a review of the disease and its treatment." *Ann. Surg. Onc.* 2006; 13(1):12-30. It is estimated that the incidence of esophageal adenocarcinoma (EA) has risen by 300-400% over the last 30 years. *NCI Cancer Bulletin* 2006; 3 (20). EA is believed to be linked to a stepwise progression through a number of pre-cancerous conditions.

Amongst risk factors it has been shown that there is a strong relationship between reflux symptoms and esophageal adenocarcinoma (Lagergren J, et al., "Symptomatic gastroesophageal reflex as a risk factor for EA." *NEJ Med.* 1999; 340:825), and the risk is further exacerbated with obesity. Barrett's metaplasia is generally accepted as the intermediate step in the development of EA and is developed as a result of gastro-esophageal reflux disease (GERD), a disease postulated to affect 20% of all U.S. adults. Estimates of the U.S. incidence of Barrett's vary between 800,000 and 2 million. However, it is reported that only 5% of EA resected patients were known to have had Barrett's Esophagus (Dulai et al., "Preoperative prevalence of BE in EA: a symptomatic review." *Gastroenterology* 2002; 122: 26-33), suggesting the ineffectiveness of current screening tools in the prediction and detection of EA. This lack of screening/detection points to the continued trend of EC to present as late stage disease and the need to provide effective treatment for this disease stage.

The American Joint Committee on Cancer designated staging of EC by tumor, node, metastasis (TMN) classification. American Joint Committee on Cancer; Esophagus. AJCC Staging Cancer Staging Manual 5$^{th}$ Ed 1992; 57. The level of tumor invasion has substantial impact on 5 year survival: T1=46%; T2=30%; T3=22%; T4=7% The node negative status also has substantial effect on those patients with resectable disease, i.e., a 40% 5 year survival in node negative case compared to 17% in node positive patients.

The treatments for EC in its various stages are well documented and include surgery, stents, dilation, radiotherapy and/or chemotherapy, including the use of docetaxel. In general, symptoms do not develop until late stage EC, by which time there are limited treatment options. It is estimated that less than 20% of patients presenting with EC survive 1 year post diagnosis and 50% of patients have metastatic disease at diagnosis and are deemed candidates for palliation.

Dysphagia is one of the most common (90%) symptoms in EC and can often lead to disruption of diet resulting in weightloss and other diet related complications. Sleisenger and Fordtran, *Gastrointestinal and Liver Disease* (7$^{th}$ Edition) Vol. 1:651. Complete esophageal obstruction as a result on tumor bulk invading the esophagus occurs in nearly all patients as they progress through the various stages of this cancer.

In the later stages of EC, treatment regimes are often only palliative and are focused on Quality of Life (QoL) issues such as nutritional needs and the ability to swallow food and/or liquids. In some late stage patients even the ability to swallow saliva is impaired. In patients with complete esophageal obstruction without evidence of metastasis, the traditional means of treating the dysphagia is surgical excision. This treatment has up to a 10% mortality rate and significant morbidity. In view of the age of many patients at presentation (median 67 year old) endoscopic palliation plays a critical role.

In an exemplary embodiment of the invention, a liposome is utilized in conjunction with a heating probe or electrode to treat esophageal cancer. Liposome formulations suitable for use in the present invention have components that include at least one amphiphile, at least one surfactant, and at least one hydrophilic polymer. The hydrophilic polymer may be unmodified; or modified by the addition of functional groups to associate with the membrane; or chemically bound to an amphiphile, surfactant, or other component of the membrane. An example of a modification to associate the hydrophilic polymer with the membrane can include the addition of a polar or charge-forming functional group to produce a stronger association with the polar group of the membrane-forming amphiphile or surfactant. The hydrophilic polymer may, alternatively, be covalently bound to the membrane-forming amphiphile or surfactant so that it is present on the surface of the liposome to protect and maintain its integrity, or it may be incorporated into the inner lipid layer of the liposome formulation. The hydrophilic polymer can be bonded to the amphiphile or surfactant through a biodegradable or hydrolysable linkage such as, for example, an amide or ester linkage, or through a more stable linkage such as an amine or ether linkage.

The ratio of amphiphile to surfactant is variable and can be any ratio that is suitable for the intended use of the liposome. It is recognized that both the amphiphile and surfactant may have amphiphilic and surface active properties; however, when both components have similar properties, for the purposes of this specification, the amphiphile can be considered as the major membrane component, while the surfactant is the minor component. Thus the ratio of amphiphile to surfactant is at least about 51:49 and can be as large as 99:1. In exemplary embodiments, the amphiphile:surfactant ratio is at least about 70:30, and can be about 80:20 or 90:10. As is known in the art, the addition of surfactant can cause variations in the physical or chemical properties of the liposome to achieve some desirable property such as a reduction in phase transition temperature or permeability of the membrane.

A hydrophilic polymer may be present in the membrane of a liposome in varying amounts ranging from about 0.1 to about 25 molar percent, based on the total amount of amphiphile and surfactant. In embodiments where the hydrophilic polymer is bound to a liposome-forming phospholipid that contains about 75-90% by weight hydrophilic polymer and 25-10% by weight lipid, this corresponds to about 0.11 to about 33 molar percent of hydrophilic polymer modified phospholipid. As will be appreciated by those skilled in the art, the conversion of molar percent hydrophilic polymer to molar percent of modified amphiphile will depend on the molecular weight of the unmodified amphiphile and the molecular weight of the hydrophilic polymer. Calculation of the ratios is well within the purview of persons skilled in the art. Embodiments of the invention can include about 3 to 20 molar percent hydrophilic polymer (for example, from about 3 to about 27 molar percent modified amphiphile) or 3 to 10 molar percent hydrophilic polymer (for example, from about 3 to about 13 molar percent modified amphiphile). Certain embodiments of the invention are prepared from about 4 to about 5 molar percent modified amphiphile, thus providing about from about 2.5 to about 4.5 molar percent hydrophilic polymer. The optimal amount of hydrophilic polymer can be determined easily through routine experimentation by persons of skill in the art.

The methods of the invention can be effective with liposomes prepared from a wide variety of compositions including, but not limited to phospholipids, soybean lipids, phosphoethanolamines, cholesterol, lysolipids, surfactants, and mixtures thereof, in combination with at least one hydrophilic polymer such as polyethylene glycol, polyacryloylmorpholine, poly-2-ethyl-2-oxazoline, polyvinylpyrrolidone, methoxypolyethylene glycol (mPEG) derivatives and mixtures thereof. Examples of the phospholipids of the invention include, but are not limited to, phosphatidyl cholines, phosphatidyl glycerols, phosphatidyl inositols, phosphatidyl ethanolamines, and sphingomyelins. Representative surfactants useful in the invention can include, but are not limited to, dichain phospholipids, lysolipids, bile acids, myristoyl surfactants, palmitoyl surfactants, stearoyl surfactants, glyceryl monooleates, ceramides, PEG-ceramides, C18-ether linked phosphatidyl choline, polyethylene glycol-polyethylene copolymers, block copolymers, fatty acids and mixtures thereof. Examples of lysolipids useful in the invention include, but are not limited to monopalmitoyl phosphatidylcholine (MPPC), monolauryl phosphatidylcholine (MLPC), monomyristoyl phosphatidylcholine (MMPC), monostearoyl phosphatidylcholine (MSPC), and mixtures thereof. Representative hydrophilic polymers useful in the invention include, but are not limited to, polyethylene glycol, polyacryloylmorpholine, poly-2-ethyl-2-oxazoline, polyvinylpyrrolidone, and methoxypolyethylene glycol (mPEG), and mixtures thereof. Examples of active agents useful in the invention include, but are not limited to, pharmacologically active agents, flavor agents, diagnostic agents, nutritional agents, gene products, non-biologically active products such as imaging agents, and mixtures thereof.

One embodiment of a thermosensitive liposome useful in this exemplary method of the invention comprises the phospholipid DPPC, the lysolipid MSPC, and a phospholipid such as 1,2-distearoyl-sn-glycero-3-phosphoethanolamine (DSPE) functionalized to include a hydrophilic polymer, for example DSPE-mPEG-2000 and/or DSPE-mPEG-5000, in which the hydrophilic polymer is attached to the lipid through an amide linkage. Liposome compositions can comprise molar ratios of phospholipid:lysolipid:hydrophilic polymer functionalized-phospholipids as low as 90:10:1 can be used. An exemplary molar ratio of phospholipid:lysolipid:hydrophilic polymer functionalized-phospholipid is about 90:10:4.

The liposome composition described above can encapsulate doxorubicin, a known anti-cancer agent. Methods for the preparation of such thermosensitive liposomes and loading the liposomes with doxorubicin have been described. For example, exemplary liposomes and their preparation are described. See; e.g., Needham, U.S. Pat. Nos. 6,200,598 and 6,726,925; Ogawa, U.S. Pat. No. 5,094,854, incorporated herein by reference.

In this exemplary embodiment the heating device can be a Stretta® system from Curon Medical, Inc. (Freemont, Calif.) The system utilizes an endoscopically-guided, minimally invasive procedure. The catheter is powered by a Curon Control Module. The catheter includes a guide wire tip to facilitate passage of the catheter to the gastro-esophageal junction and a balloon supports precise delivery of submucosal needles. The catheter can include four channels and can monitor the temperature of the target tissue, as well as tissue impedance. A pump delivers chilled water via catheter ports adjacent to the site of needle entry to preserve the integrity of the surrounding tissue that is not being treated.

According to this exemplary embodiment of the invention, a composition that includes a thermosensitive liposome encapsulating an antineoplastic agent, for example doxorubicin, is administered to the subject in need of treatment. The thermosensitive liposome can be administered systemically, for example by I.V. Alternatively, the thermosensitve liposome can be administered local in the area near the tumor. Local administration can be intravenously, intra-arterially or inter-tumorally. Initiation of administration of the thermosensitive liposome composition can begin prior to heat therapy or treatment, for example, from about 15 minutes to about 30 minutes prior to heat therapy. Administration of the thermosensitive liposome composition can terminate prior to heat therapy or continue for some period of overlap with the heat therapy or continue throughout heat therapy.

To administer the heat, a catheter containing a heating device is inserted through the mouth of a subject, for example, a human patient, and into the esophagus. The heating device can include one or more probes or electrodes, depending in the size of the tumor or area to be treated. The probe is positioned at the site of the tumor and at least one of the probes inserted into the tumor location. The positioned probe is energized to create a heated area utilizing, for example, radio frequency energy. In the case of a catheter containing multiple probes, it may be possible to control energization of the probes individually. In such a case, only those probes that are actually positioned in the tumor tissue are energized. The temperature of the probe is adjusted to give the desired heating profile, i.e., the temperature of the probe(s) and the time at which the probe is held at this temperature is adjusted to achieve a suitable heat profile. A suitable heat profile is one in which the tissue area is heated, which can include the tumor mass and tumor margins, and achieves a temperature sufficient to release an active agent from a thermosensitive liposome or activate a thermo-activated drug.

The temperature of the probe is adjusted to achieve the desired heat profile. In the case of the symptomatic treatment of esophageal cancer, it may not be desirable to heat the probe to a temperature high enough to achieve tumor ablation. The temperature should be high enough to achieve release of the active agent. This can be achieved by heating the probe to a temperature of about 45° C. to about 50° C. The probe can be energized until the tissue surrounding the probe reaches a desired temperature. The temperature of the surrounding tissue can be monitored by a sensing probe in the catheter as described above. When the tissue reaches the desired temperature, energy to the probe can be cycled off. If the temperature of the surrounding tissue decrease below the desired temperature during treatment, the probe can be re-energized to keep the temperature within a desired range. As an alternative to this on/off cycling, the energy to the probe may be pulsed to maintain the desired temperature range throughout the treatment. In order to achieve treatment throughout the tumor mass, the catheter or probes can be rotated or moved in and out, and inserted in different parts of the tumor as infusion of the liposome continues.

In the case of esophageal cancer, the present method is useful for symptomatic treatment rather than as a curative measure. That is, the goal of the therapy may be to reduce tumor size and thus improve quality of life by increasing the patient's ability to swallow; the prognosis for survival by victims of esophageal cancer is generally not favorable. Thus, treatment can be repeated as necessary to control tumor size and esophageal obstruction as measured by monitoring dysphagia.

Using the present methodology for tumors in general, the tumor mass and, if desired, margins are heated to a temperature sufficient to release the active agent from the liposome when the liposomes are in the tumor and/or at the tumor margins. This method can have several effects. For example, heat can be applied in such a way that there is sufficient heat at the tumor mass to cause ablation of the tumor. At the tumor margins, the heat may be insufficient to cause ablation, i.e. less than about 50° C. to about 55° C., but sufficient to cause release of the active agent from the liposome, for example, above about 39° C., less than about 45° C.; in the range of from about 40° C. to about 44° C.; in the range of from about 40° C. to about 43° C.; in the range of from about 39° C. to about 41° C.; in the range of from or about 40° C. to about 42° C.; in the range of from about 40° C. to about 50° C.; or in the range of from about 40° C. to about 55° C. Thus, a localized release of active agent occurs at the margins of the tumor. In another example, no tissue, including the tumor mass is heated to a temperature sufficient to cause ablation. Rather, the entire local area is heated only to a temperature sufficient to cause release of the active agent from the liposome, e.g., to a temperature between about 40° C. and about 50° C. In this example, the only treatment is by release of active agent at the tumor sites and margins.

The invention is further illustrated by the following non-limiting examples:

Example 1

Modeling of Heating

A. Phantom Study

Figure 13:
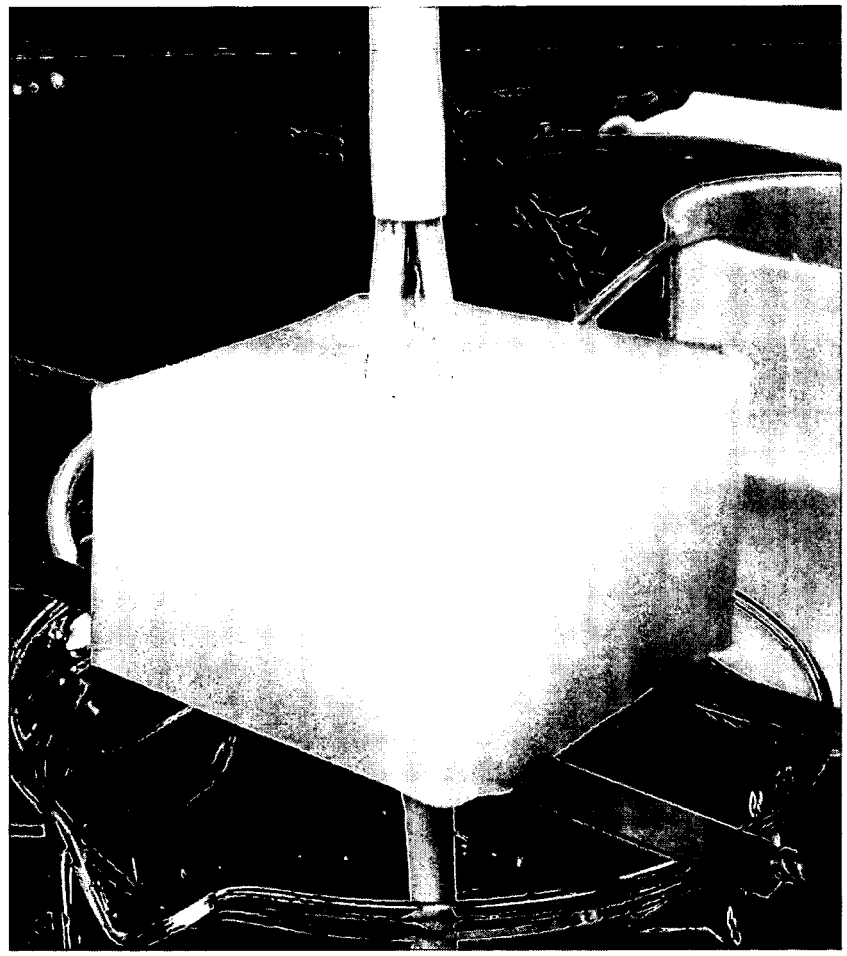
FIG. 13 illustrates an experimental set up for phantom studies to validate mathematical models.

To validate the computer models, a study in phantoms made of Agar (5%), NaCl (0.25%), Albumin (0.5%), and water was performed. These phantoms reproduce thermal and electrical tissue properties, and coagulate at 75° C. Phantoms were created with 2.5 cm diameter cylindrical holes approximating esophageal dimensions. The setup is shown in FIG. 13. After ablation, the phantom was sliced to determine dimensions of the coagulated regions.

Figure 14:
FIG. 14 illustrates an axial slice of the coagulation zone achieved in a phantom study.
Figure 15:
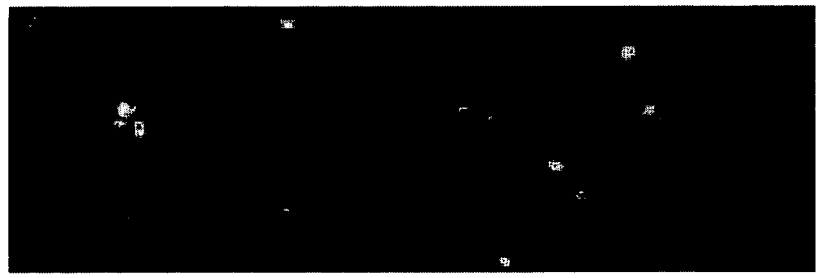
FIG. 15 illustrates a radial slice of three coagulation zones achieved in a phantom study.

A 90° C. electrode temperature was maintained for 2 minutes to obtain larger coagulation zones (clinically, 80-85° C. and 1 min are used). FIGS. 14 and 15 show coagulation zones (i.e., zones>75° C.) from these experiments. On average, the 75° C. boundary was ~2 mm in diameter (FIG. 15).

B. Computer Models

Figure 16A:
FIG. 16a illustrates a model of a catheter.
Figure 16B:
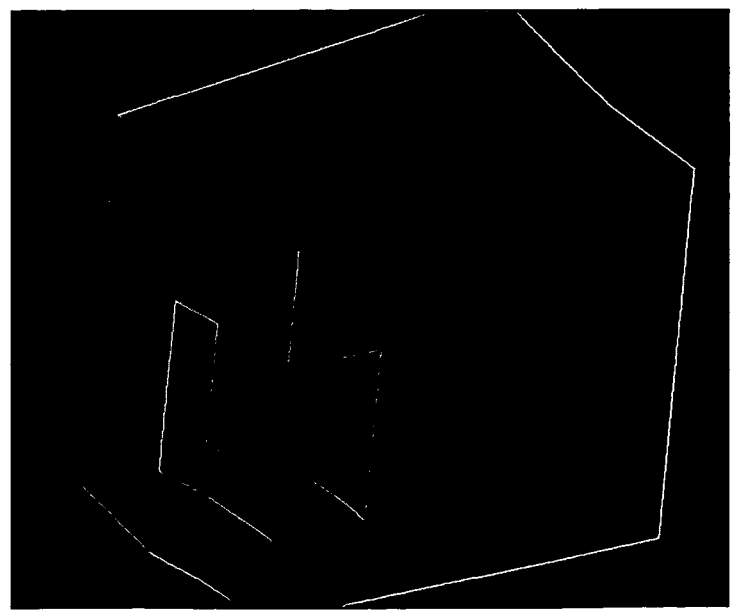
FIG. 16b illustrates a model of a catheter inserted into the lumen of an esophagus.

Geometrically accurate models of the Stretta catheter needle (FIG. 16a, left) were created. The needle was inserted into tissue inside the simulated esophageal lumen (FIG. 16). The lumen was filled with saline solution, since saline is circulated during the procedure to cool the esophageal surface. From patient data provided by Curon, the needle temperature outside tissue is typically between 28-30° C. Convectional cooling was applied in the models to reproduce these temperatures. Initial models were compared to phantom experiments above and showed same diameter (~2 mm) of the 75° C.-isotherm.

During the procedure, applied power was controlled such that the electrode tip temperature is kept at a constant operator-defined temperature, typically 80° C. Ablation was simulated for 1 min (clinically used time), at different electrode temperatures of 45° C., 50° C., 60° C., 70° C. and 80° C. Images showing axial temperature distribution with isotherms from 40-50° C. in 1° C.-intervals are shown in FIGS. 17-21 from electrode temperatures of 45° C., 50° C., 60° C., 70° C. and 80° C., respectively.

Figure 17:
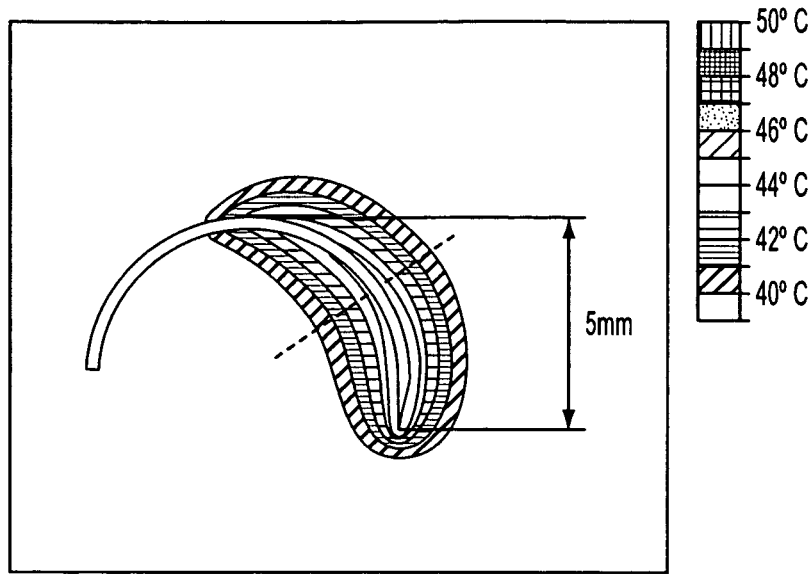
FIGS. 17-21 illustrate axial temperature profiles in tissue models from electrode temperatures of 45° C., 50° C., 60° C., 70° C. and 80° C., respectively.
Figure 18:
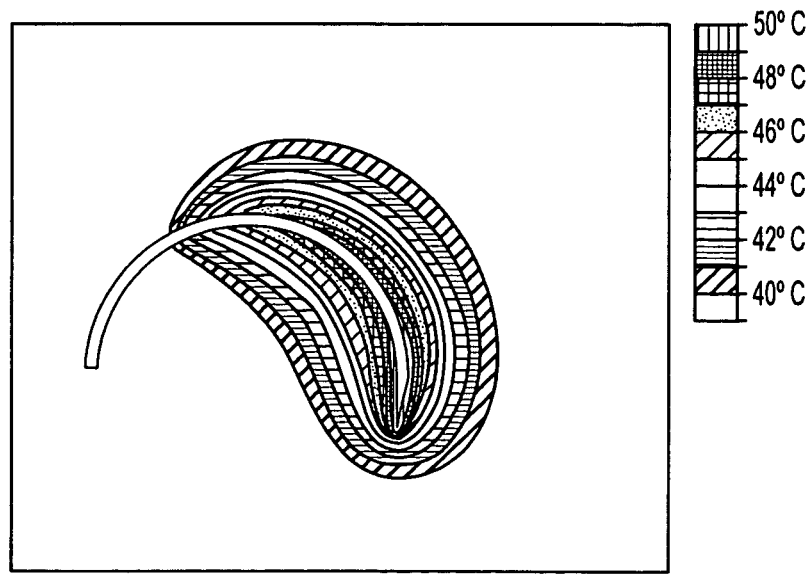
Figure 19:
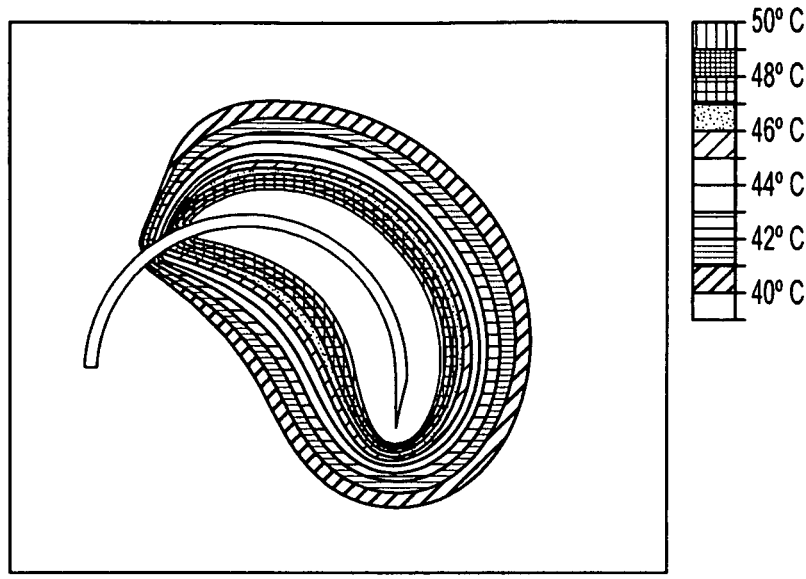
Figure 20:
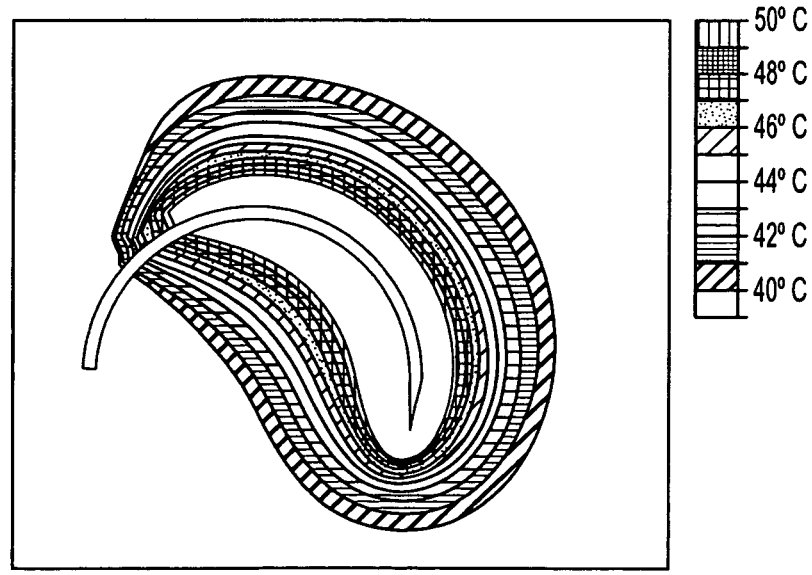
Figure 21:
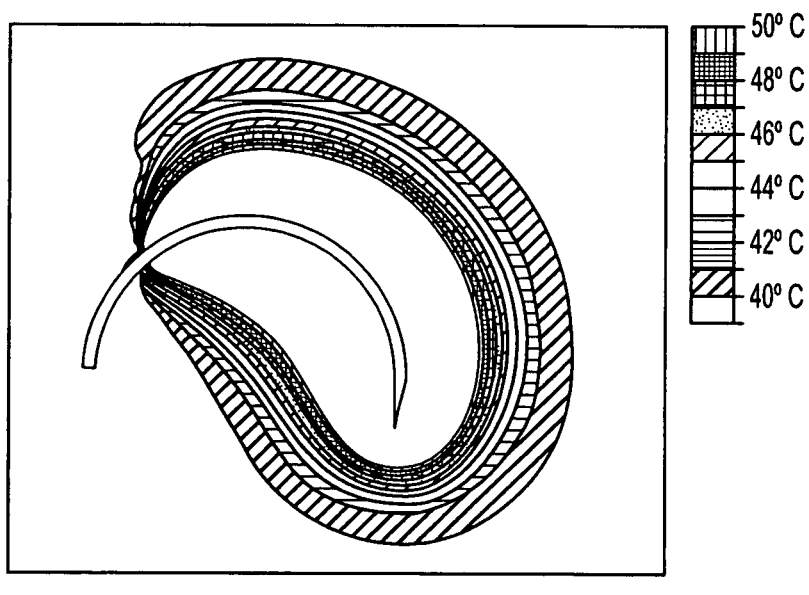

The table below shows diameters of 40° C. and 50° C. isotherms along white dotted line in FIG. 17.

| Electrode temperature | 50° C.-isotherm (mm) | 40° C.-isotherm (mm) |
|---|---|---|
| 45° C. | 0 | 4.5 |
| 50° C. | 0 | 7.4 |
| 60° C. | 3.6 | 9.9 |
| 70° C. | 4.8 | 10 |
| 80° C. | 6.9 | 13.2 |

Example 2

Testing Protocol

Three dosage levels are used that comprise a thermosensitive liposome prepared from DPPC, MSPC, and DSPE in a molar ratio of about 90:10:4. Doxorubicin is encapsulated within the liposomes. The three dose levels are about 20, 30, 40 mg/m² doxorubicin. The thermosensitive liposome is infused over 30 minutes; the RF heating procedure begins approximately 15 minutes after start of the infusion.

The RF heating procedure is designed to create local tissue temperatures above 40° C. to a depth of at least 3 cm measured from the deepest portion of the tumor. Temperature is maintained below locally ablative temperatures. Under endoscopic guidance, the catheter is placed in the center of greatest tumor mass. As many of the catheter heating prongs as possible are deployed directly into the tumor.

This procedure is repeated at approximately 21 day intervals or as tolerated. Therapy continues unless: 1) there is a complete pathological response, 2) there are safety issues precluding further therapy, 3) there is disease progression, or 4) the patient withdraws from the study.

Therapy recipients are monitored throughout administration and for 24 hours thereafter. After the 24 hour post-treatment assessments, recipients are scheduled for follow up visits on Day 7 (±3 days), and Day 14 (±3 days). Repeat therapy initiates a new cycle conducted as above.

Endoscopy with ultrasound is be used to determine the local effectiveness of the therapy with regards to tumor appearance, local response and histopathology. Additional testing, including CT scans is obtained as clinically indicated to assess tumor response. The primary assessment of effectiveness is based on dysphagia symptom scores obtained from patient questionnaires (on an ordinal scale rated from 1 (Patient can swallow all solids) to 5 (Patient can swallow no liquids))

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

I claim:

1. A method of treating cancer comprising:
   inserting into a cancerous tissue a distal end portion of a catheter defining a lumen, the catheter comprising a distal tip adapted to penetrate tissue, at least one catheter port located at the distal tip, and a plurality of probes disposed within the lumen, each of the plurality of probes comprising a distal tip adapted to penetrate tissue;
   extending at least two of the plurality of probes such that a portion of each of the at least two probes is disposed outside the lumen extending into the cancerous tissue, at least one of the at least two probes is individually extended into the cancerous tissue;
   delivering a liposome containing an active agent or a thermo-activated drug, gene or virus to the cancerous tissue via the catheter port; and
   individually energizing at least one of the at least two probes extended into the cancerous tissue such that the at least two probes:
   introduce heat to an outer zone of tissue, the outer zone of tissue including a margin of the cancerous tissue, the heat introduced to the outer zone of tissue sufficient to release the active agent or activate the thermo-activated drug, gene or virus, the heat introduced to the outer zone of tissue causing a temperature of the outer zone of tissue to be no greater than about 45° C.; and
   introduce heat to an inner zone of tissue, the inner zone of tissue disposed between the outer zone of tissue and the plurality of probes, the inner zone of tissue being comprised of the cancerous tissue, the heat introduced to the inner zone of tissue sufficient to thermally ablate at least a portion of the cancerous tissue of the inner zone of tissue, the heat introduced to the inner zone of tissue causing a temperature of the cancerous tissue of the inner zone of tissue to be at least about 50° C.

2. The method of claim 1, wherein the heat is delivered to at least one of the outer zone of tissue or the inner zone of tissue after the delivery of the liposome or thermo-activated drug, gene or virus.

3. The method of claim 1, wherein the liposome containing an active agent or a thermo-activated drug, gene or virus is a thermosensitive liposome.

4. The method of claim 3, wherein the thermosensitive liposome contains an anti-neoplastic agent.

5. The method of claim 4, wherein the anti-neoplastic agent is doxorubicin.

6. The method of claim 1, wherein the temperature of at least one of the at least two probes introducing heat to the inner zone of tissue is between about 80° C. and about 90° C.

7. The method of claim 1, wherein the heat is introduced to cancerous tissue within at least one of the outer zone of tissue or the inner zone of tissue using a dynamic heat control to deliver heat over a temperature range.

8. The method of claim 1, wherein the heat introduced to the outer zone of tissue causes the temperature of the outer zone of tissue to be within a temperature range from about 39° C. to about 41° C.

9. The method of claim 1, wherein the heat introduced to the outer zone of tissue causes the temperature of the outer zone of tissue to be within a temperature range from about 40° C. to about 42° C.

10. The method of claim 1, wherein the heat introduced to the outer zone of tissue causes the temperature of the outer zone of tissue to be within a temperature range from about 40° C. to about 55° C.

11. The method of claim 1, wherein the heat introduced to the inner zone of tissue causes the temperature of the inner zone of tissue to be within a temperature range from about 50° C. to about 55° C.

12. The method of claim 7, wherein the liposome containing an active agent or a thermo-activated drug, gene or virus is a thermosensitive liposome.

13. The method of claim 12, wherein the thermosensitive liposome contains an anti-neoplastic agent.

14. The method of claim 13, wherein the anti-neoplastic agent is doxorubicin.

15. The method of claim 13, wherein the at least two probes extending into the cancerous tissue introduce heat to the cancerous tissue within at least the outer zone of tissue or the inner zone of tissue until a temperature of the cancerous tissue within at least the outer zone of tissue or the inner zone of tissue reaches a predetermined temperature, and further the at least two of the plurality of probes reapply heat to the cancerous tissue within at least the outer zone of tissue or the inner zone of tissue when the temperature of the cancerous tissue within at least the outer zone of tissue or the inner zone of tissue is less than the predetermined temperature.

16. The method of claim 15, wherein at least one of the introducing heat or the reapplying heat includes providing a pulsing energy to the cancerous tissue.

17. The method of claim 13, wherein the temperature of the heat introduced is increased until a temperature of a portion of the cancerous tissue furthest from the at least two probes reaches a predetermined temperature.

18. The method of claim 13, further comprising:
adjusting a length of a portion of at least one probe of the at least two probes disposed outside the lumen.

19. A method of treating cancer comprising:
delivering a liposome containing an active agent or a thermo-activated drug, gene or virus into a target treatment area including a cancerous tissue via a catheter defining a lumen, the catheter comprising a distal tip adapted to penetrate tissue, at least one catheter port located at the distal tip, and a plurality of probes disposed within the lumen, each of the plurality of probes comprising a distal tip adapted to penetrate tissue, the liposome being delivered into the target treatment area via the catheter port;
determining the size of the target treatment area including the cancerous tissue, the determining including 1) extending at least two probes outside of the lumen into the target treatment area, at least one of the at least two probes is individually extended, and 2) heating the target treatment area, prior to the delivering, via individually energizing at least one of the at least two probes to a temperature sufficient to release the active agent or activate the thermo-activated drug, gene or virus, and
increasing the temperature of the target treatment area via individually energizing at least one of the at least two probes, after the delivering, over a period of time such that a portion of the cancerous tissue a first distance from the probes reaches a predetermined temperature subsequent a portion of the cancerous tissue a second distance from the probes.

20. The method of claim 19, wherein the temperature is increased until a temperature of a portion of the cancerous tissue furthest from the probes reaches the predetermined temperature.

21. The method of claim 19, the method further comprising adjusting a length of a portion of the at least one of the at least two probes disposed outside the lumen based on the size of the target treatment area including the cancerous tissue.

22. A method of treating cancer comprising:
inserting a distal end portion of a catheter into a cancerous tissue, the distal end of the catheter comprising a distal tip adapted to penetrate tissue and a first conduit located at the distal tip, the catheter defining a second conduit comprising a plurality of probes, each of the plurality of probes comprising a distal tip adapted to penetrate tissue;
delivering a liposome containing an active agent or a thermo-activated drug, gene or virus into the cancerous tissue via the first conduit defined by the distal tip of the catheter;
heating a first treatment zone of the cancerous tissue to a temperature sufficient to release the active agent or activate the thermo-activated drug, gene or virus by introducing energy to the cancerous tissue via a first probe individually extended at least partially outside of the second conduit into the cancerous tissue;
heating a second treatment zone of the cancerous tissue to a temperature sufficient to thermally ablate the cancerous tissue of the second treatment zone by introducing energy to the cancerous tissue via a second probe individually extended at least partially outside of the second conduit into the cancerous tissue, the second treatment zone different than the first treatment zone; and
monitoring a temperature at each of the first treatment zone and the second treatment zone of the cancerous tissue via temperature readings from a third conduit defined by the catheter.

23. The method of claim 22, wherein a temperature of a portion of the cancerous tissue adjacent the distal end portion of the catheter is increased until a temperature of a portion of the cancerous tissue furthest from the distal end portion of the catheter reaches a predetermined temperature.

24. The method of claim 22, further comprising:
introducing a cooled fluid to the cancerous tissue via the first conduit.

25. The method of claim 22, further comprising:
determining the size of a target treatment area including the cancerous tissue prior to the delivering the liposome, the determining including heating the target treatment area prior to the delivering.

26. The method of claim 22, wherein the energy introduced to the cancerous tissue is pulsed to maintain the temperature of at least one of the first treatment zone or the second treatment zone of the cancerous tissue at a predetermined temperature.

* * * * *